US009480572B2

(12) United States Patent
Jodaitis et al.

(10) Patent No.: US 9,480,572 B2
(45) Date of Patent: Nov. 1, 2016

(54) INTERVERTEBRAL DISC PROSTHESIS INSERTION ASSEMBLIES

(71) Applicant: LDR Medical, Rosières Près Troyes (FR)

(72) Inventors: Alexandre Jodaitis, Morlanwelz (BE); Herve Dinville, St-Parres-Aux-Tertres (FR); Alexis Mercier, Troyes (FR)

(73) Assignee: LDR Medical, Sainte-Savine (FR)

( * ) Notice: Subject to any disclaimer, the term of this patent is extended or adjusted under 35 U.S.C. 154(b) by 0 days.

(21) Appl. No.: 13/919,704

(22) Filed: Jun. 17, 2013

(65) Prior Publication Data

US 2013/0282124 A1     Oct. 24, 2013

Related U.S. Application Data

(63) Continuation of application No. 11/676,237, filed on Feb. 16, 2007, now Pat. No. 8,465,546.

(51) Int. Cl.
*A61F 2/44* (2006.01)
*A61F 2/46* (2006.01)
(Continued)

(52) U.S. Cl.
CPC .............. *A61F 2/442* (2013.01); *A61F 2/4425* (2013.01); *A61F 2/4611* (2013.01); *A61F 2/0095* (2013.01); *A61F 2002/3071* (2013.01); *A61F 2002/30607* (2013.01); *A61F 2002/30616* (2013.01);
(Continued)

(58) Field of Classification Search
CPC ............ A61F 2/44–2/447; A61F 2/46; A61F 2/4611

USPC .......... 623/17.11–17.16; 606/86 A, 86 R, 99
See application file for complete search history.

(56) References Cited

U.S. PATENT DOCUMENTS 5,306,309 A * 4/1994 Wagner et al. ............ 623/17.16
5,443,514 A   8/1995 Steffee
(Continued)

FOREIGN PATENT DOCUMENTS

WO    WO03099172    12/2003
WO    WO2005007044    1/2005
(Continued)

OTHER PUBLICATIONS

Apparatus and Method for Fusing Opposing Spinal Vertebrae, Bramlet, Dale G. et al., U.S. Appl. No. 09/635,436, filed Aug. 11, 2000.
(Continued)

*Primary Examiner* — Jan Christopher Merene
*Assistant Examiner* — Steven Cotroneo
(74) *Attorney, Agent, or Firm* — Lauff Law PLLC

(57) ABSTRACT

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various other embodiments, the prosthesis and an insertion tool are provided in a sterile pack, with the prosthesis components and the insertion tool sterilized and packaged in one or more types or layers of sterile packaging.

20 Claims, 11 Drawing Sheets

(51) Int. Cl.
*A61F 2/00* (2006.01)
*A61F 2/30* (2006.01)

(52) U.S. Cl.
CPC ............ *A61F2002/30617* (2013.01); *A61F 2002/30662* (2013.01); *A61F 2002/30711* (2013.01); *A61F 2002/30714* (2013.01); *A61F 2002/30904* (2013.01); *A61F 2002/443* (2013.01); *A61F 2002/4622* (2013.01); *A61F 2002/4627* (2013.01); *A61F 2002/4628* (2013.01); *A61F 2002/4681* (2013.01); *A61F 2250/0062* (2013.01); *A61F 2250/0085* (2013.01); *A61F 2250/0086* (2013.01); *A61F 2250/0089* (2013.01); *A61F 2250/0097* (2013.01)

(56) References Cited

U.S. PATENT DOCUMENTS

| | | | |
|---|---|---|---|
| 5,723,013 | A * | 3/1998 | Jeanson et al. ............ 623/17.16 |
| 6,540,753 | B2 | 4/2003 | Cohen |
| 6,599,294 | B2 | 7/2003 | Fuss et al. |
| 7,147,665 | B1 | 12/2006 | Bryan et al. |
| 7,217,292 | B2 * | 5/2007 | Ralph ................ A61B 17/025 606/99 |
| 7,404,795 | B2 * | 7/2008 | Ralph et al. ................. 600/219 |
| 7,419,505 | B2 * | 9/2008 | Fleischmann et al. .... 623/17.11 |
| 7,481,840 | B2 | 1/2009 | Zuckerman et al. |
| 7,494,507 | B2 | 2/2009 | Dixon et al. |
| 7,517,363 | B2 | 4/2009 | Rogers et al. |
| 7,575,599 | B2 | 8/2009 | de Villiers et al. |
| 7,575,600 | B2 | 8/2009 | Zuckerman et al. |
| 7,611,538 | B2 | 11/2009 | Belliard et al. |
| 7,621,956 | B2 | 11/2009 | Paul et al. |
| 7,708,776 | B1 | 5/2010 | Blain et al. |
| 7,717,959 | B2 | 5/2010 | William et al. |
| 7,771,478 | B2 | 8/2010 | Navarro et al. |
| 7,896,919 | B2 | 3/2011 | Belliard et al. |
| 8,257,439 | B2 | 9/2012 | Zeegers |
| 8,267,999 | B2 | 9/2012 | Beaurain et al. |
| 8,343,219 | B2 | 1/2013 | Allain et al. |
| 8,388,684 | B2 | 3/2013 | Bao et al. |
| 8,439,931 | B2 | 5/2013 | Dinville |
| 8,465,546 | B2 | 6/2013 | Jodaitis et al. |
| 8,685,100 | B2 | 4/2014 | Jodaitis et al. |
| 8,753,397 | B2 | 6/2014 | Beaurain et al. |
| 8,771,284 | B2 | 7/2014 | Rashbaum et al. |
| 8,858,635 | B2 | 10/2014 | Hovorka et al. |
| 2002/0035400 | A1 | 3/2002 | Bryan et al. |
| 2002/0070565 | A1 | 6/2002 | Szapucki et al. |
| 2002/0161375 | A1 * | 10/2002 | Ralph et al. ............. 606/99 |
| 2003/0069586 | A1 * | 4/2003 | Errico et al. ............. 606/99 |
| 2004/0243240 | A1 * | 12/2004 | Beaurain et al. .......... 623/17.14 |
| 2005/0038516 | A1 | 2/2005 | Spoonamore |
| 2005/0197706 | A1 * | 9/2005 | Hovorka ............... A61F 2/4425 623/17.15 |
| 2006/0030860 | A1 * | 2/2006 | Peterman ................ 606/99 |
| 2006/0116768 | A1 * | 6/2006 | Krueger et al. ........... 623/17.14 |
| 2006/0259147 | A1 | 11/2006 | Krishna et al. |
| 2007/0088362 | A1 * | 4/2007 | Bonutti ............. A61B 17/0218 606/99 |
| 2007/0162130 | A1 * | 7/2007 | Rashbaum ........... A61F 2/4425 623/17.11 |
| 2007/0162137 | A1 | 7/2007 | Kloss et al. |
| 2007/0168040 | A1 * | 7/2007 | Raymond ................. 623/17.15 |
| 2007/0208345 | A1 * | 9/2007 | Marnay et al. ............. 606/61 |
| 2007/0293948 | A1 * | 12/2007 | Bagga et al. ............. 623/17.11 |
| 2008/0262504 | A1 * | 10/2008 | Ralph et al. ............. 606/99 |
| 2009/0005874 | A1 * | 1/2009 | Fleischmann et al. .... 623/17.16 |
| 2012/0116466 | A1 | 5/2012 | Dinville et al. |
| 2012/0330424 | A1 | 12/2012 | Zeegers |
| 2013/0013006 | A1 | 1/2013 | Rashbaum et al. |
| 2013/0150968 | A1 | 6/2013 | Dinville et al. |
| 2013/0166029 | A1 | 6/2013 | Dinville et al. |
| 2013/0226300 | A1 | 8/2013 | Chataigner et al. |
| 2013/0253648 | A1 | 9/2013 | Beaurain et al. |
| 2013/0253651 | A1 | 9/2013 | Dinville |
| 2013/0282124 | A1 | 10/2013 | Jodaitis et al. |
| 2014/0114413 | A1 | 4/2014 | Allain et al. |

FOREIGN PATENT DOCUMENTS

| | | |
|---|---|---|
| WO | WO2005063150 | 7/2005 |
| WO | WO2013124453 | 8/2013 |

OTHER PUBLICATIONS

Intervertebral nucleus prosthesis and surgical procedure for implanting the same, Gau, Michel, U.S. Appl. No. 10/060,862, filed Jan. 30, 2002.

Intersomatic cage with unified grafts, Huppert, Jean, U.S. Appl. No. 10/276,712, filed Mar. 26, 2003.

Spinal Osteosynthesis Device and Preparation Method, Beaurain, Jacques et al., U.S. Appl. No. 10/473,999, filed Apr. 12, 2004.

Intervertebral Disc Prosthesis and Fitting Tools, Beaurain, Jacques et al., U.S. Appl. No. 10/476,565, filed Jun. 8, 2004.

Vertebral Cage Device With Modular Fixation, Louis, Christian et al., U.S. Appl. No. 10/483,563, filed May 21, 2004.

Progressive approach osteosynthesis device and preassembly method, Delecrin, Joel et al., U.S. Appl. No. 10/492,753, filed Aug. 9, 2004.

Plate for osteosynthesis device and method of preassembling such device, Delecrin, Joel et al., U.S. Appl. No. 10/492,827, filed Jul. 15, 2004.

Osseous anchoring device for a prosthesis, Huppert, Jean et al., U.S. Appl. No. 10/494,418, filed Jul. 22, 2004.

Implant for Osseous Anchoring with Polyaxial Head, Beaurain, Jacques et al., U.S. Appl. No. 10/498,234, filed Dec. 7, 2004.

Intervertebral Disk Prosthesis, Beaurain, Jacques et al., U.S. Appl. No. 10/533,846, filed Nov. 11, 2005.

Osseous anchoring implant with a polyaxial head and method for installing the implant, Renaud, Christian et al., U.S. Appl. No. 10/570,080, filed Jun. 9, 2006.

Device and method for sectioning a vertebral lamina, Mangione, Paolo, U.S. Appl. No. 10/575,065, filed May 30, 2006.

Intervertebral Disc Prosthesis, Hovorka, Istvan et al., U.S. Appl. No. 11/051,710, filed Feb. 4, 2005.

Intervertebral Disc Prosthesis, Zeegers, M. Willem, U.S. Appl. No. 11/098,266, filed Apr. 4, 2005.

Intervertebral Disc Prosthesis, Zeegers, M. Willem, U.S. Appl. No. 11/109,276, filed Apr. 18, 2005.

Instrumentation and Methods for Inserting an Intervertebral Disc Prosthesis, Dinville, Herve, U.S. Appl. No. 11/180,868, filed Jul. 13, 2005.

Intervertebral Disc Prosthesis, Rashbaum, Ralph et al., U.S. Appl. No. 11/341,007, filed Jan. 27, 2006.

Intervertebral Disc Prosthesis and Instrumentation for Insertion of the Prosthesis Between the Vertebrae, Rashbaum, Ralph et al., U.S. Appl. No. 11/362,253, filed Feb. 24, 2006.

Transforanimal intersomatic cage for an intervertebral fusion graft and an instrument for implanting the cage, Davis, Reginald James et al., U.S. Appl. No. 11/378,165, filed Mar. 17, 2006.

Intervertebral nucleus prosthesis and surgical procedure for implanting the same, Gau, Michel, U.S. Appl. No. 11/390,711, filed Mar. 27, 2006.

Intervertebral disc prosthesis insertion assemblies, Jodaitis, Alexandre et al., U.S. Appl. No. 11/676,237, filed Feb. 16, 2007.

Intersomatic cage with unified grafts, Huppert, Jean, U.S. Appl. No. 11/767,386, filed Jun. 22, 2007.

Modular intervertebral prosthesis, Vila, Thierry et al., U.S. Appl. No. 11/874,144, filed Oct. 17, 2007.

Vertebral Support Device, Cho, Paul et al., U.S. Appl. No. 11/958,285, filed Dec. 17, 2007.

Intervertebral disc prosthesis, surgical methods, and fitting tools, Beaurain, Jacques et al., U.S. Appl. No. 12/025,677, filed Feb. 4, 2008.

(56) References Cited

OTHER PUBLICATIONS

Intersomatic cage, intervertebral prosthesis, anchoring device and implantation instruments, Allain, Jerome et al., U.S. Appl. No. 12/134,884, filed Jun. 6, 2008.
Transverse spinal linking device and system, Paul Cho et al., U.S. Appl. No. 12/172,074, filed Jul. 11, 2008.
Transforaminal intersomatic cage for an intervertebral fusion graft and an instrument for implanting the cage, Davis, Reginald James et al., U.S. Appl. No. 12/279,664, filed Apr. 22, 2009.
Intervertebral Disc Prosthesis, Zeegers, M. Willem, U.S. Appl. No. 12/360,050, filed Jan. 26, 2009.
Intervertebral Disc Prosthesis, Zeegers, M. Willem, U.S. Appl. No. 12/391,086, filed Feb. 23, 2009.
Spinal Osteosynthesis Device and Preparation Method, Beaurain, Jacques et al., U.S. Appl. No. 12/409,327, filed Mar. 23, 2009.
Intervertebral disc prosthesis, Beaurain, Jacques et al., U.S. Appl. No. 12/424,364, filed Apr. 15, 2009.
Vertebral Cage Device With Modular Fixation, Louis, Christian et al., U.S. Appl. No. 12/430,768, filed Apr. 27, 2009.
Instrumentation and Methods for Inserting an Intervertebral Disc Prosthesis, Dinville, Herve, U.S. Appl. No. 12/435,955, filed May 5, 2009.
Intervertebral disc prosthesis insertion assemblies, Jodaitis, Alexandre et al., U.S. Appl. No. 12/527,373, filed Mar. 19, 2010.
Intervertebral Disc Prosthesis, Rashbaum, Ralph et al., U.S. Appl. No. 12/955,898, filed Nov. 29, 2010.
Instruments and Methods for Removing Fixation Devices from Intervertebral Implants, Dinville, Herve et al., U.S. Appl. No. 13/158,761, filed Jun. 13, 2011.
Intervertebral Disc Prosthesis, Zeegers, M. Willem, U.S. Appl. No. 13/215,123, filed Aug. 22, 2011.
Interspinous Implant and Implantation Instrument, Dinville, Hervéet al., U.S. Appl. No. 13/369,650, filed Feb. 9, 2012.
Vertebral Cage Device With Modular Fixation, Louis, Christian et al., U.S. Appl. No. 13/438,352, filed Apr. 3, 2012.
Plate for osteosynthesis device and method of preassembling such device, Delecrin, Joel et al., filed 13/454,927, filed Apr. 24, 2012.
Anchoring Device and System for an Intervertebral Implant, Intervertebral Implant and Implantation Instrument, Dinville, Hervéet al., U.S. Appl. No. 13/520,041, filed Nov. 26, 2012.
Anchoring Device and System for an Intervertebral Implant, Intervertebral Implant and Implantation Instrument, Dinville, Hervéet al., U.S. Appl. No. 13/538,078, filed Jun. 29, 2012.
Transforaminal intersomatic cage for an intervertebral fusion graft and an instrument for implanting the cage, Davis, Reginald James et al., U.S. Appl. No. 13/585,063, filed Aug. 14, 2012.
Intervertebral Disc Prosthesis, Zeegers, M. Willem, U.S. Appl. No. 13/603,043, filed Sep. 4, 2012.
Intervertebral Disk Prosthesis, Beaurain, Jacques et al., U.S. Appl. No. 13/616,448, filed Sep. 14, 2012.
Intervertebral Disc Prosthesis and Instrumentation for Insertion of the Prosthesis Between the Vertebrae, Rashbaum, Ralph et al., U.S. Appl. No. 13/620,797, filed Sep. 15, 2012.
Intersomatic cage, intervertebral prosthesis, anchoring device and implantation instruments, Allain, Jerome et al., U.S. Appl. No. 13/732,244, filed Dec. 31, 2012.
Anchoring device and system for an intervertebral implant, intervertebral implant and implantation instrument, Chataigner, Hervéet al., U.S. Appl. No. 13/774,547, filed Feb. 22, 2013.
Transforanimal intersomatic cage for an intervertebral fusion graft and an instrument for implanting the cage, Davis, Reginald James et al., U.S. Appl. No. 13/854,808, filed Apr. 1, 2013.
Spinal Osteosynthesis Device and Preparation Method, Beaurain, Jacques et al., U.S. Appl. No. 13/873,190, filed Apr. 29, 2013.
Instrumentation and Methods for Inserting an Intervertebral Disc Prosthesis, Dinville, Herve, U.S. Appl. No. 13/892,933, filed May 13, 2013.
Intervertebral disc prosthesis insertion assemblies, Jodaitis, Alexandre et al., U.S. Appl. No. 13/919,704, filed Jun. 17, 2013.
Interspinous Implant and Implantation Instrument, Dinville, Hervéet al., U.S. Appl. No. 14/130,286, filed Jul. 3, 2014.
Intersomatic cage with unified grafts, Huppert, Jean, U.S. Appl. No. 14/149,357, filed Jan. 7, 2014.
Nucleus Prostheses, Vila, Thierry et al., U.S. Appl. No. 14/159,161, filed Jan. 20, 2014.
Intervertebral disc prosthesis insertion assemblies, Jodaitis, Alexandre et al., U.S. Appl. No. 14/242,177, filed Apr. 1, 2014.
Vertebral implant, vertebral fastening device of the implant and implant instrumentation, Dinville, Hervéet al., U.S. Appl. No. 14/246,442, filed Apr. 7, 2014.
Interspinous Implant and Implantation Instrument, Dinville, Hervéet al., U.S. Appl. No. 14/252,754, filed Apr. 14, 2014.
Anchoring device for a spinal implant, spinal implant and implantation instrumentation, HervéChataigner et al., U.S. Appl. No. 14/252,852, filed Apr. 15, 2014.
Intervertebral Disk Prosthesis, Beaurain, Jacques et al., U.S. Appl. No. 14/306,785, filed Jun. 17, 2014.
Intervertebral Disc Prosthesis and Instrumentation for Insertion of the Prosthesis Between the Vertebrae, Rashbaum, Ralph et al., U.S. Appl. No. 14/325,317, filed Jul. 7, 2014.
Anchoring device and system for an intervertebral implant, intervertebral implant and implantation instrument, Chataigner, Hervéet al., U.S. Appl. No. 14/380,714, filed Aug. 23, 2014.
Osseous anchoring implant with a polyaxial head and method for installing the implant, Renaud, Christian et al., U.S. Appl. No. 14/497,321, filed Sep. 26, 2014.
Intervertebral Disc Prosthesis, Hovorka, Istvan et al., U.S. Appl. No. 14/513,818, filed Oct. 14, 2014.
LDR Medical, by its attorneys; Interview Summary in U.S. Appl. No. 12/527,373, filed Jan. 31, 2014; USPTO; Alexandria, Virginia; All Pages.
U.S. Patent & Trademark Office; Notice of Allowance in U.S. Appl. No. 12/527,373; Dec. 24, 2013; USPTO; Alexandria, Virginia; All Pages.
LDR Medical, by its attorneys; Request for Continued Examination in U.S. Appl. No. 12/527,373, filed Dec. 2, 2013; USPTO; Alexandria, Virginia; All Pages.
U.S. Patent & Trademark Office; Notice of Allowance in U.S. Appl. No. 12/527,373; Aug. 30, 2013; USPTO; Alexandria, Virginia; All Pages.
U.S. Patent & Trademark Office; Interview Summary in U.S. Appl. No. 12/527,373, filed Aug. 30, 2013; USPTO; Alexandria, Virginia; All Pages.
LDR Medical, by its attorneys; Appeal Brief in U.S. Appl. No. 12/527,373, filed Apr. 24, 2013; USPTO; Alexandria, Virginia; All Pages.
U.S. Patent & Trademark Office; Office Action in U.S. Appl. No. 12/527,373; Sep. 24, 2012; USPTO; Alexandria, Virginia; All Pages.
U.S. Patent & Trademark Office; Office Action in U.S. Appl. No. 11/341,007; Apr. 13, 2009; USPTO; Alexandria, Virgina; All Pages.
U.S. Patent & Trademark Office; Office Action in U.S. Appl. No. 12/025,677; Nov. 7, 2014; USPTO; Alexandria, Virgina; All Pages.
U.S. Patent & Trademark Office; Reply to Office Action in U.S. Appl. No. 12/025,677; Aug. 19, 2014; USPTO; Alexandria, Virgina; All Pages.
U.S. Patent & Trademark Office; Reply to Office Action in U.S. Appl. No. 12/025,677; Feb. 19, 2014; USPTO; Alexandria, Virgina; All Pages.
LDR Medical, by its attorneys; Reply to Office Action in U.S. Appl. No. 12/025,677; Dec. 20, 2013; USPTO; Alexandria, Virgina; All Pages.
U.S. Patent & Trademark Office; Office Action in U.S. Appl. No. 12/025,677; Jun. 20, 2013; USPTO; Alexandria, Virgina; All Pages.
LDR Medical, by its attorneys; Reply to Office Action in U.S. Appl. No. 12/025,677; Dec. 29, 2012; USPTO; Alexandria, Virginia; All Pages.
U.S. Patent & Trademark Office; Notice of Allowance in U.S. Appl. No. 12/424,364; Aug. 2, 2012; USPTO; Alexandria, Virginia; All Pages.

(56) References Cited

OTHER PUBLICATIONS

U.S. Patent & Trademark Office; Notice of Allowance in U.S. Appl. No. 13/616,448; Feb. 7, 2014; USPTO; Alexandria, Virginia; All Pages.
U.S. Patent & Trademark Office; Office Action in U.S. Appl. No. 13/616,448; Aug. 22, 2013; USPTO; Alexandria, Virginia; All Pages.
U.S. Patent & Trademark Office; Office Action in U.S. Appl. No. 14/306,785; Oct. 22, 2014; USPTO; Alexandria, Virginia; All Pages.
U.S. Patent & Trademark Office; Notice of allowance in U.S. Appl. No. 11/051,710; Jun. 11, 2014; USPTO; Alexandria, Virginia; All Pages.
LDR Medical, by its attorneys; Request for Continued Examination in U.S. Appl. No. 11/051,710; Jul. 11, 2013; USPTO; Alexandria, Virginia; All Pages.
U.S. Patent & Trademark Office; Notice of Allowance in U.S. Appl. No. 11/051,710; Apr. 11, 2013; USPTO; Alexandria, Virgina; All Pages.
LDR Medical, by its attorneys; Appeal Brief in U.S. Appl. No. 11/051,710; Jan. 15, 2013; USPTO; Alexandria, Virgina; All Pages.
U.S. Patent & Trademark Office; Notice of Allowance in U.S. Appl. No. 13/215,123; Aug. 29, 2014; USPTO; Alexandria, Virgina; All Pages.
LDR Medical, by its attorneys; Reply to Office Action in U.S. Appl. No. 13/215,123; May 19, 2014; USPTO; Alexandria, Virgina; All Pages.
U.S. Patent & Trademark Office; Office Action in U.S. Appl. No.13/215,123; Nov. 18, 2013; USPTO; Alexandria, Virgina; All Pages.
LDR Medical, by its attorneys; Reply to Office Action in U.S. Appl. No. 13/215,123; Nov. 11, 2013; USPTO; Alexandria, Virginia; All Pages.
LDR Medical, by its attorneys; Reply to Office Action in U.S. Appl. No. 13/215,123; Oct. 24, 2013; USPTO; Alexandria, Virginia; All Pages.
U.S. Patent & Trademark Office; Office Action in U.S. Appl. No. 13/215,123; May 24, 2013; USPTO; Alexandria, Virginia; All Pages.
LDR Medical, by its attorneys; Reply to Office Action in U.S. Appl. No. 13/215,123; Mar. 23, 2013; USPTO; Alexandria, Virginia; All Pages.
LDR Medical, by its attorneys; Terminal Disclaimer in U.S. Appl. No. 13/215,123; Mar. 20, 2013; USPTO; Alexandria, Virginia; All Pages.
U.S. Patent & Trademark Office; Office Action in U.S. Appl. No. 13/215,123; Nov. 20, 2012; USPTO; Alexandria, Virgina; All Pages.
U.S. Patent & Trademark Office; Notice of Allowance in U.S. Appl. No. 12/360,050; Aug. 2, 2012; USPTO; Alexandria, Virgina; All Pages.
U.S. Patent & Trademark Office; Notice of Allowance in U.S. Appl. No. 12/360,050; May 18, 2012; USPTO; Alexandria, Virgina; All Pages.
U.S. Patent & Trademark Office; Office Action in U.S. Appl. No. 13/603,043; Jul. 24, 2014; USPTO; Alexandria, Virgina; All Pages.
LDR Medical, by its attorneys; Reply to Office Action in U.S. Appl. No. 13/603,043; May 21, 2014; USPTO; Alexandria, Virgina; All Pages.
U.S. Patent & Trademark Office; Office Action in U.S. Appl. No. 13/603,043; Nov. 21, 2013; USPTO; Alexandria, Virgina; All Pages.
LDR Medical, by its attorneys; Reply to Office Action in U.S. Appl. No. 13/603,043; Oct. 9, 2013; USPTO; Alexandria, Virgina; All Pages.
U.S. Patent & Trademark Office; Office Action in U.S. Appl. No. 13/603,043; Apr. 9, 2013; USPTO; Alexandria, Virgina; All Pages.
U.S. Patent & Trademark Office; Notice of Allowance in U.S. Appl. No. 12/435,955; Jan. 16, 2013; USPTO; Alexandria, Virgina; All Pages.
LDR Medical, by its attorneys; Reply to Office Action in U.S. Appl. No. 12/435,955; Dec. 24, 2012; USPTO; Alexandria, Virginia; All Pages.
U.S. Patent & Trademark Office; Office Action in U.S. Appl. No. 12/435,955; Jul. 23, 2012; USPTO; Alexandria, Virginia; All Pages.
U.S. Patent & Trademark Office; Office Action in U.S. Appl. No. 13/892,933; Jul. 28, 2014; USPTO; Alexandria, Virginia; All Pages.
LDR Medical, by its attorneys; Reply to Office Action in U.S. Appl. No. 13/892,933; Apr. 2, 2014; USPTO; Alexandria, Virginia; All Pages.
U.S. Patent & Trademark Office; Office Action in U.S. Appl. No. 13/892,933; Jan. 2, 2014; USPTO; Alexandria, Virginia; All Pages.
U.S. Patent & Trademark Office; Notice of Allowance in U.S. Appl. No. 12/955,898; Aug. 8, 2014; USPTO; Alexandria, Virginia; All Pages.
LDR Medical, by its attorneys; Reply to Office Action in U.S. Appl. No. 12/955,898; Aug. 4, 2014; USPTO; Alexandria, Virginia; All Pages.
U.S. Patent & Trademark Office; Office Action in U.S. Appl. No. 12/955,898; Mar. 3, 2014; USPTO; Alexandria, Virgina; All Pages.
LDR Medical, by its attorneys; Reply to Office Action in U.S. Appl. No. 12/955,898; Jul. 10, 2013; USPTO; Alexandria, Virginia; All Pages.
U.S. Patent & Trademark Office; Office Action in U.S. Appl. No. 12/955,898; Jan. 10, 2013; USPTO; Alexandria, Virgina; All Pages.
LDR Medical, by its attorneys; Reply to Office Action in U.S. Appl. No. 12/955,898; Dec. 3, 2012; USPTO; Alexandria, Virginia; All Pages.
LDR Medical, by its attorneys; Reply Brief in U.S. Appl. No. 11/362,253; Aug. 20, 2012; USPTO; Alexandria, Virgina; All Pages.
U.S. Patent & Trademark Office; Notice of Allowance in U.S. Appl. No. 13/620,797; Jan. 29, 2014; USPTO; Alexandria, Virgina; All Pages.
LDR Medical, by its attorneys; Reply to Office Action in U.S. Appl. No. 13/620,797; Nov. 5, 2013; USPTO; Alexandria, Virginia; All Pages.
U.S. Patent & Trademark Office; Office Action in U.S. Appl. No. 13/620,797; Jul. 5, 2013; USPTO; Alexandria, Virgina; All Pages.
U.S. Patent & Trademark Office; Notice of Allowance in U.S. Appl. No. 10/533,846; Nov. 4, 2009; USPTO; Alexandria, Virginia; All Pages.
LDR Medical, by its attorneys; Reply to Office Action in U.S. Appl. No. 10/533,846; Apr. 15, 2009; USPTO; Alexandria, Virginia; All Pages.
U.S. Patent & Trademark Office; Office Action in U.S. Appl. No. 10/533,846; Oct. 15, 2008; USPTO; Alexandria, Virginia; All Pages.
LDR Medical, by its attorneys; Reply to Office Action in U.S. Appl. No. 10/533,846; Jun. 25, 2008; USPTO; Alexandria, Virginia; All Pages.
U.S. Patent & Trademark Office; Office Action in U.S. Appl. No. 10/533,846; Dec. 26, 2007; USPTO; Alexandria, Virgina; All Pages.
LDR Medical, by its attorneys; Reply to Office Action in U.S. Appl. No. 10/533,846; Oct. 16, 2007; USPTO; Alexandria, Virginia; All Pages.
U.S. Patent & Trademark Office; Office Action in U.S. Appl. No. 10/533,846; Apr. 18, 2007; USPTO; Alexandria, Virginia; All Pages.
U.S. Patent & Trademark Office; Notice of Allowance in U.S. Appl. No. 11/109,276; Dec. 8, 2009; USPTO; Alexandria, Virgina; All Pages.
LDR Medical, by its attorneys; Reply to Office Action in U.S. Appl. No. 11/109,276; Aug. 4, 2009; USPTO; Alexandria, Virginia; All Pages.
U.S. Patent & Trademark Office; Office Action in U.S. Appl. No. 11/109,276; Feb. 13, 2009; USPTO; Alexandria, Virgina; All Pages.
LDR Medical, by its attorneys; Reply to Office Action in U.S. Appl. No. 11/109,276; Jan. 26, 2009; USPTO; Alexandria, Virginia; All Pages.
U.S. Patent & Trademark Office; Office Action in U.S. Appl. No. 11/109,276; Jul. 24, 2008; USPTO; Alexandria, Virginia; All Pages.
LDR Medical, by its attorneys; Reply to Office Action in U.S. Appl. No. 11/109,276; Apr. 16, 2008; USPTO; Alexandria, Virginia; All Pages.

(56) References Cited

OTHER PUBLICATIONS

U.S. Patent & Trademark Office; Office Action in U.S. Appl. No. 11/109,276; Oct. 16, 2007; USPTO; Alexandria, Virginia; All Pages.
LDR Medical, by its attorneys; Reply to Office Action in U.S. Appl. No. 11/109,276; Aug. 6, 2007; USPTO; Alexandria, Virginia; All Pages.
U.S. Patent & Trademark Office; Office Action in U.S. Appl. No. 11/109,276; Feb. 6, 2007; USPTO; Alexandria, Virgina; All Pages.
U.S. Patent & Trademark Office; Notice of Allowance in U.S. Appl. No. 11/180,868; Jul. 31, 2009; USPTO; Alexandria, Virgina; All Pages.
U.S. Patent & Trademark Office; Notice of Allowance in U.S. Appl. No. 11/180,868; Jul. 17, 2009; USPTO; Alexandria, Virgina; All Pages.
LDR Medical, by its attorneys; Reply to Office Action in U.S. Appl. No. 11/180,868; May 5, 2009; USPTO; Alexandria, Virgina; All Pages.
U.S. Patent & Trademark Office; Office Action in U.S. Appl. No. 11/180,868; Nov. 5, 2008; USPTO; Alexandria, Virgina; All Pages.
LDR Medical, by its attorneys; Reply to Office Action in U.S. Appl. No. 11/180,868; Jul. 21, 2008; USPTO; Alexandria, Virgina; All Pages.
U.S. Patent & Trademark Office; Office Action in U.S. Appl. No. 11/180,868; Jan. 22, 2008; USPTO; Alexandria, Virgina; All Pages.
European Patent Office; search report in Application No. 13170071, Pub. No. EP2633835; Oct. 1, 2013; European Patent Office; Munich, Germany; All Pages.
European Patent Office; search report in Application No. 10185004, Pub. No. EP2327375; Apr. 6, 2011; European Patent Office; Munich, Germany; All Pages.
European Patent Office; Notice of Intention to Grant a European Patent for Pub'n No. EP1711133, App'n No. EP050702425; Oct. 22, 2010; EPO; Munich, Germany; all pages.
European Patent Office; Office Action for Pub'n No. EP1711133, App'n No. EP050702425; Mar. 2, 2009; EPO; Munich, Germany; all pages.
LDR Medical, by its attorneys; Reply to Office Action for Pub'n No. EP1711133, App'n No. EP050702425; Jul. 22, 2009; EPO; Munich, Germany; all pages.
European Patent Office; Office action in Application No. 11165170, Pub. No. EP2363080; May 15, 2012; European Patent Office; Munich, Germany; All Pages.
European Patent Office; Office action and search report in Application No. 11165170, Pub. No. EP2363080; Jul. 21, 2011; European Patent Office; Munich, Germany; All Pages.
European Patent Office; Office action and search report in Application No. 05857774, Pub. No. EP1845903; Apr. 11, 2011; European Patent Office; Munich, Germany; All Pages.
European Patent Office; Office action and search report in Application No. 05857774, Pub. No. EP1845903; May 6, 2009; European Patent Office; Munich, Germany; All Pages.
LDR Medical, by its attorneys; Amendments and Reply in European Patent Application No. 11165170, Pub. No. EP2363080; Mar. 6, 2012; European Patent Office; Munich, Germany; All Pages.
LDR Medical, by its attorneys; Amendments and Reply in European Patent Application No. 05857774, Pub. No. EP1845903; Oct. 11, 2011; European Patent Office; Munich, Germany; All Pages.
LDR Medical, by its attorneys; Amendments and Reply in European Patent Application No. 05857774, Pub. No. EP1845903; Nov. 13, 2009; European Patent Office; Munich, Germany; All Pages.
LDR Medical, by its attorneys; Chapter II amendments for PCT Pub'n No. WO2006120505, App. No. PCT/IB2005/004093; Oct. 30, 2006; WIPO; Geneva, Switzerland; All Pages.

* cited by examiner

INTERVERTEBRAL DISC PROSTHESIS INSERTION ASSEMBLIES

CROSS REFERENCE TO RELATED APPLICATIONS

This application is a continuation of U.S. patent application Ser. No. 11/676,237 filed Feb. 16, 2007, and issuing as U.S. Pat. No. 8,465,546 on Jun. 18, 2013, which is incorporated herein by reference for all purposes.

BACKGROUND

A healthy intervertebral disc is flexible enough to allow movement between adjacent vertebrae or between a vertebra and another adjacent spinal column element, such as the coccyx (the most inferior portion of the vertebral column, resulting from the fusion of the four coccygeal vertebrae) and the sacrum (a triangular bone that is the posterior skeletal element forming the pelvis, formed by 5 fused vertebrae). This movement accommodates bending of the spine. Disease or degeneration of the tissues of a natural intervertebral disc often leads to intense pain and reduced mobility. When degeneration or disease of the natural intervertebral disc has progressed to the point where non-operative care such as medication, injections, and/or physical therapy is ineffective, surgical intervention may be required.

A common procedure for treatment of degenerative or diseased intervertebral discs involves removal of the natural tissues of the disc and fusion of the adjacent vertebrae. Fusion eliminates the mobility between the adjacent vertebrae, however, and can transfer stresses and movements to the intervertebral discs above and/or below the point of fusion.

Intervertebral disc prostheses have been developed to mitigate some of the problems caused by intervertebral fusion. In particular, various designs of intervertebral disc prostheses can provide a relatively normal range of movement to the adjacent vertebra, resulting in a more normal distribution of stresses and movements along the various segments of the spine. Intervertebral disc prostheses typically are configured to restore normal disc height, and can decrease surgical morbidity and complications from postoperative immobilization instrumentation typically present in fusion procedures.

U.S. patent application Nos. 10/476,565, 10/533,846, 11/051,710, and 11/362,253, each of which is assigned to the assignee of the present application and each of which is incorporated herein by reference for all purposes, disclose various intervertebral disc prosthesis configurations. In many of these configurations, the prosthesis may have an upper plate supporting the upper vertebra, a lower plate supporting the lower vertebra, and a mobile core or nucleus that provides some range of articulation between the upper plate and the lower plate.

Prior to the surgical implantation procedure, measurements often are made of the plates of the upper and lower vertebrae to confirm the viability of the procedure. Following discectomy in various representative procedures, the depth and width of the intervertebral space are measured, and a determination is made of an appropriate vertical spacing of the adjacent vertebra and the sizes of the upper and lower disc prosthesis plates and the core.

Typically, there are several selections for the depth and width of the intervertebral prosthesis plates and for the height of the core, depending on the type of intervertebral disc prosthesis. For example, the LDR Medical Mobi-C™ cervical disc prosthesis currently can be configured with any of 4 plate sizes and 3 core heights, and the LDR Medical Mobidisc™ lumbar disc prosthesis currently can be configured with any of 18 plate sizes and 6 core heights. In addition, the surgeon may wish to accommodate or correct a lordosis or kyphosis by using one or more plates having an angular offset between the vertebral axis implied by a normal to the plate's vertebral contact surface and a mean, or neutral, normal axis implied by the plate's core contact surface. Thus, even within a single product line, there may be numerous combinations of individual disc prosthesis elements available to suit the requirements of a particular patient.

In various intervertebral prosthesis product systems, the upper plates, the lower plates, and the cores are provided to the sterile field of the surgical suite individually. Once the proper configuration of the upper plate, the lower plate, and the core has been determined, typically the surgical staff must acquire the proper upper plate, lower plate, and core from inventory.

The components of the prosthesis typically are then assembled for mounting with or loading into a prosthesis insertion tool, or assembled directly with the insertion tool. In some systems, an assembly stand or jig is used for assembling the prosthesis components and loading the assembled prosthesis into an insertion tool. The selection and assembly process can be time consuming and awkward, potentially resulting in delays during the surgical proceeding. Handling of the components during assembly process can compromise the sterility of the prosthesis, and the use of additional handling equipment, such as an assembly stand or jig, can require further sterilization procedures, increase the complexity of the procedure, and clutter the surgical suite.

In some systems, an assortment of insertion tools are each configured for use with a single size or a limited range of sizes of the various prosthesis component combinations. Generally, the required size and configuration of the various prosthesis components will not be known until the surgical procedure has commenced. Thus, the surgeon will have to select the proper insertion tool during the procedure, following the determination of the proper sizes and configurations of the various prostheses components. The surgical staff therefore must disinfect and sterilize several insertion tools to have a full selection of the insertion tools at hand during the procedure. During the procedure, selection of the appropriate tool and confirmation of the selection will add to the duration and complexity of the surgical procedure. In various designs of insertion tools, however, the operative components of the insertion tool body are the same regardless of the prosthesis configuration, and only the tool's insertion adapter (for example, a head, holder, or other carrier of the assembled prosthesis) differs among the various insertion tools. Often, the differences among the various insertion adapters are dictated solely by the differences in sizes and configurations of the prosthesis components.

SUMMARY

In various embodiments, an intervertebral disc prosthesis is provided. The prosthesis may be provided with an insertion adapter, such as a head, holder, or other carrier of the prosthesis. The insertion adapter may be configured to retain the prosthesis and to engage an insertion tool body. In various embodiments, the prosthesis and the insertion holder are provided in a sterile pack, with the prosthesis components and the insertion holder sterilized and packaged in one or more types or layers of sterile packaging. In various embodiments, the prosthesis and an insertion tool are provided in a sterile pack, with the prosthesis components and the insertion holder sterilized and packaged in one or more types or layers of sterile packaging. Intervertebral disc prosthesis insertion assemblies, intervertebral disc prosthesis insertion systems, intervertebral disc prosthesis delivery and insertion systems, methods of inserting an intervertebral disc prosthesis between adjacent elements of a spinal column, methods of inserting an intervertebral disc prosthesis between adjacent elements of a spinal column, and methods of aseptically delivering an intervertebral disc prosthesis insertion assembly to a sterile field are also disclosed.

DETAILED DESCRIPTION OF VARIOUS EMBODIMENTS

Figure 1:
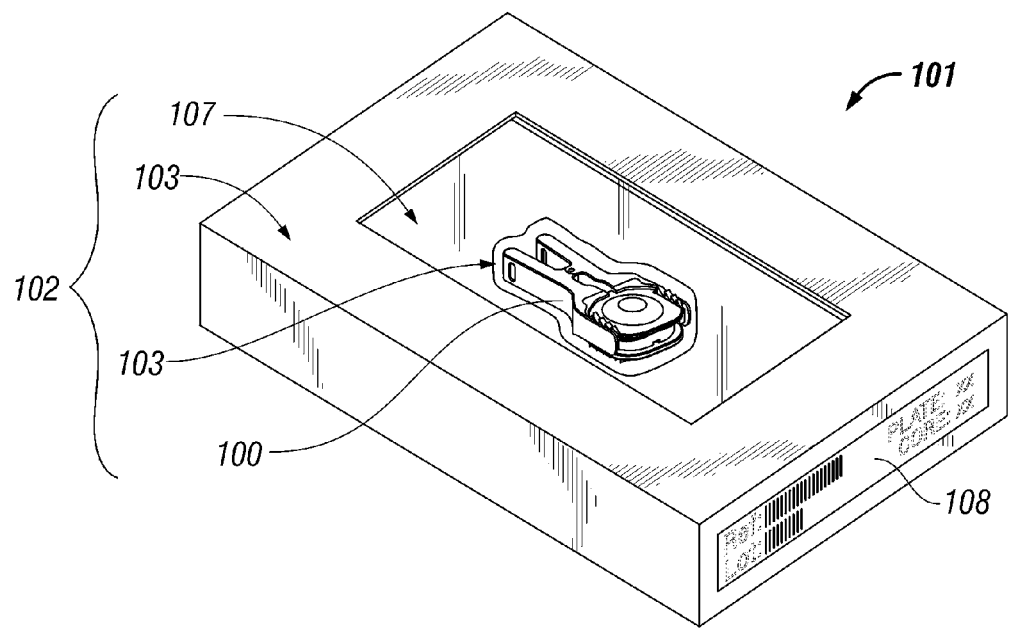
FIG. 1 depicts a sterile pack comprising a prosthesis insertion assembly.
Figure 2:
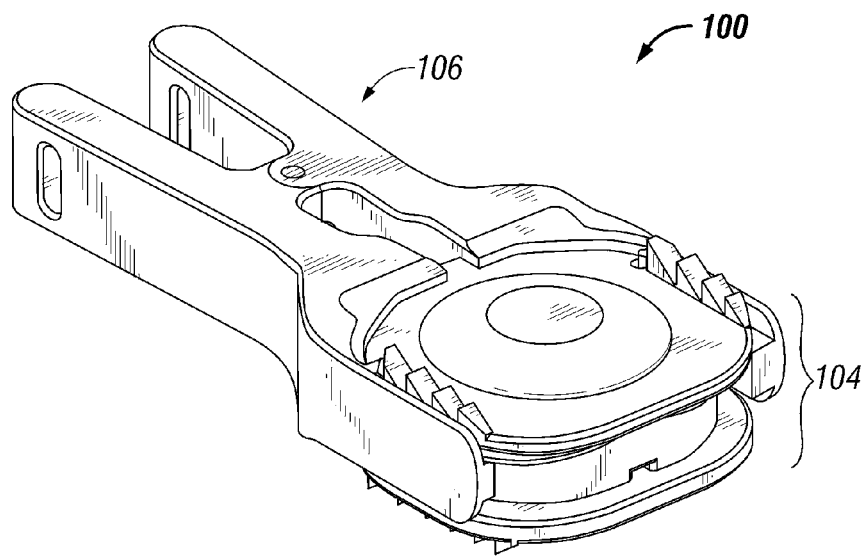
FIG. 2 depicts a prosthesis insertion assembly.

FIG. 1 depicts one of many possible embodiment of a packaged intervertebral disc prosthesis insertion assembly (101). In this embodiment, a sterile insertion adapter (106) and sterile components of an intervertebral disc prosthesis (104) may be assembled together to form a sterile prosthesis insertion assembly (100) as shown in FIG. 2, which is disposed in primary, or inner, sterile packaging (103) and in secondary, or outer, sterile packaging (103) to form a sterile pack (102). The components of the intervertebral disc prosthesis (104) may be assembled with the insertion adapter (106) and provided to the sterile field of a surgical suite pre-configured and ready to use.

FIG. 2 depicts one of many potential embodiments of an insertion assembly (100). Various embodiments of the insertion assembly (100) may comprise an intervertebral disc prosthesis (104) of the type manufactured by LDR Medical, Inc., and an insertion adapter (106), which holds the prosthesis (104) and couples with, mounts to, or otherwise joins or engages a detachable or demountable surgical tool body (130), for example as illustrated in FIG. 4, used in implanting the prosthesis (104). In this embodiment, a clip (126), for example as illustrated in FIG. 3, provides additional restraint to the components of prosthesis (104).

Figure 3:
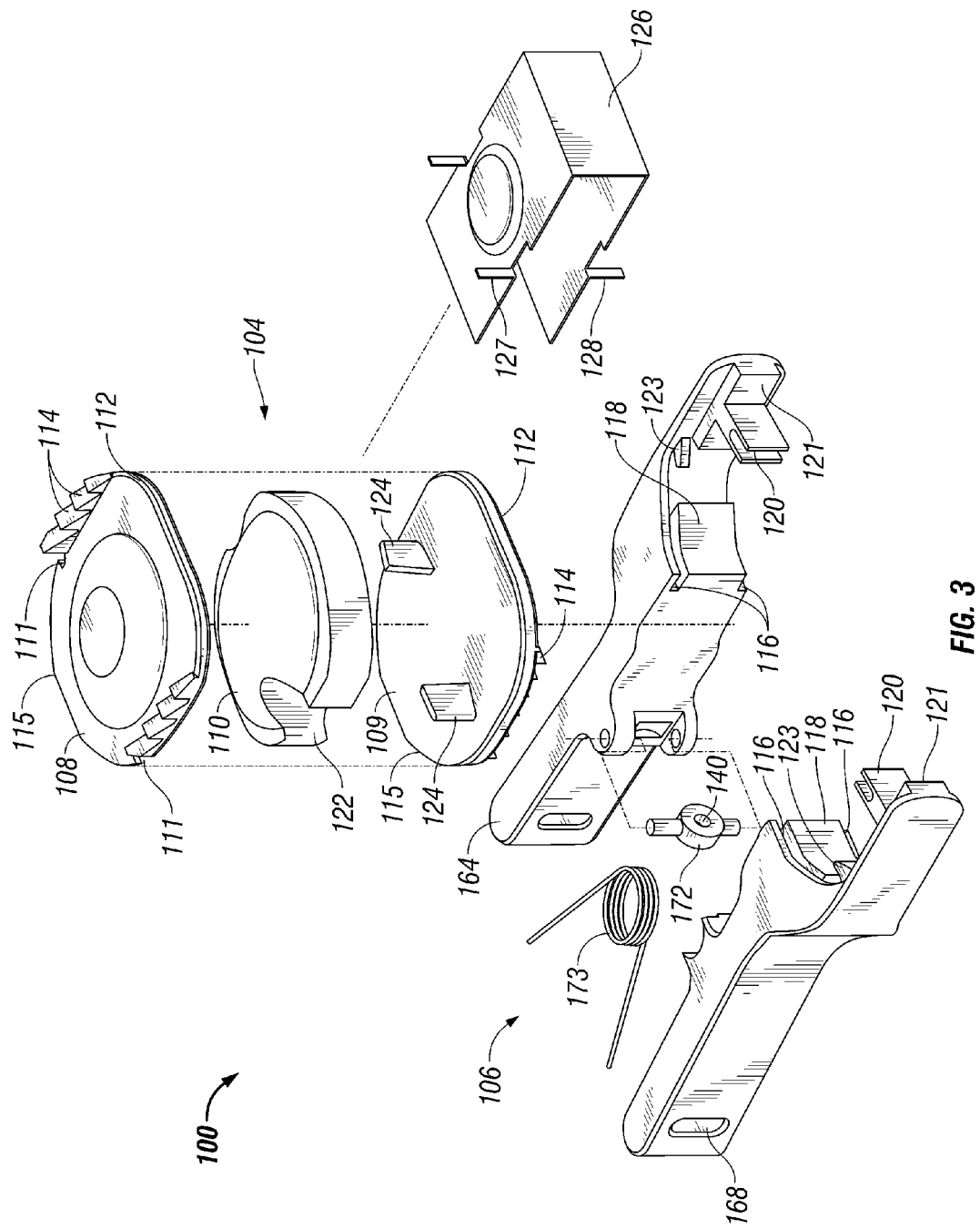
FIG. 3 depicts details of a prosthesis insertion assembly.
Figure 4:
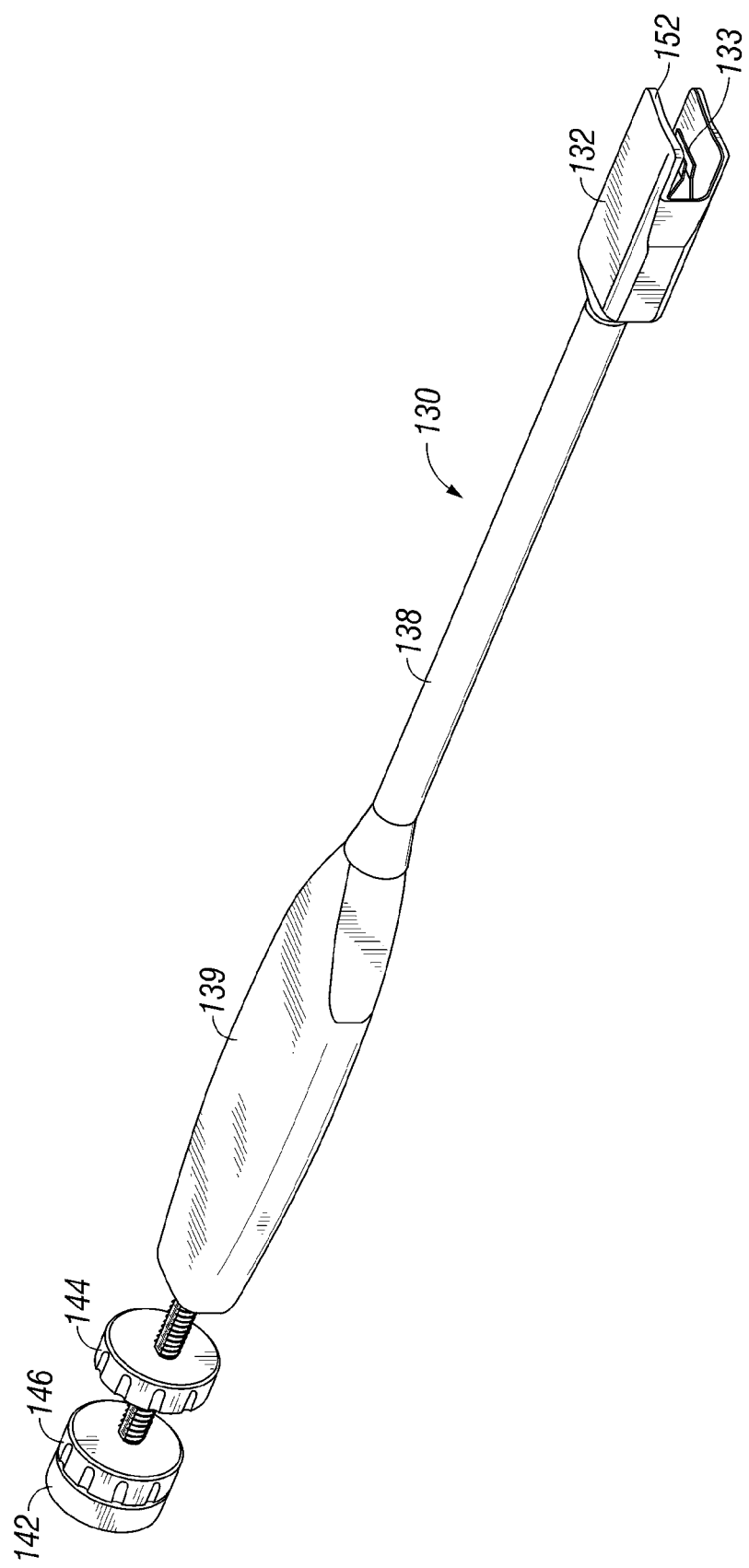
FIG. 4 depicts an insertion tool body.

FIG. 3 shows an exploded view of an embodiment of a prosthesis (104) and an insertion adapter (106). The prosthesis (104) in this embodiment comprises a first plate, such as upper plate (108), a second plate, such as lower plate (109), and a mobile core (110). The configurations of "upper" and "lower" plates generally are reversible, and the designation of the plates as "first" and "second," of course, is purely arbitrary. The upper and lower plates (108, 109) preferably may be made of chromium, cobalt, and molybdenum, but other compositions may used. In various preferred embodiments, the core may be made of an ultrahigh molecular weight polyethylene. A titanium and hydroxyapatite plasma spray coating may optionally be applied to the vertebral contact surfaces of the upper and lower plates (108, 109) to encourage at least partial fusion with the adjacent vertebrae by bony ingrowth or other forms of adhesion.

The prosthesis (104) in various embodiments may contain other features. For example, second plate (109) may be configured with core-travel stops, for example posts (124) as illustrated, that limit the translational and rotational movement of core (110). In such embodiments, contact between the stops (124) and the recesses (122) along the perimeter of the core body may be configured to limit the translational and rotational movement of the core (110). The plates (108, 109) optionally may have angled edges (115) configured for complementary contact with optional angled contact surfaces (116) of the insertion adapter (106), the benefits of which are described in greater detail below.

Additional optional features of the prosthesis (104) may facilitate implantation of the prosthesis and its stability once implanted. For example, one or more of the edges of the prosthesis (104) that encounter the surfaces of the vertebrae (150) during prosthesis insertion may be beveled, for example edges (112) of the upper plate (108) and the lower plate (109), which may reduce the effort required to insert the prosthesis (104). Alternate embodiments may not contain this bevel at all, or may be beveled in only a few strategic locations around the perimeter of the plates (108, 109). Various embodiments also may have anchors (114) that, for example, may comprise notches or teeth disposed on either or both of the plates (108, 109) in the region of one or more edges of the prosthesis (104), or one or more anchors may be elsewhere along either or both of the vertebral contact surfaces of the plates (108, 109). The anchors (114) may be configured in such a way that they minimize the force required during the implantation of the prosthesis (104), while opposing subsequent movement of the prosthesis. After the prosthesis (104) is implanted, anchors (114) preferably stabilize the prosthesis (104) and oppose movement relative to the vertebrae (150) in multiple ways. For example, the anchors (114) may provide teeth opposing movement, primarily in the direction of removal, between the prosthesis (104) and the vertebrae (150), thus helping to keep the prosthesis (104) in place after implantation and during withdrawal of the insertion adapter (106). The surfaces of the plates (108, 109) also may have a porous biocompatible coating, for example as described above, that also allows adhesion of the osseous tissue and its fusion with the prosthesis. Once osseous tissue has adhered to the plates (108, 109) and grown around the anchors (114), a strong connection may be formed between each of the plates (108, 109) of the prosthesis (104) and the respective adjacent vertebra (150). In alternate embodiments, the porous, biocompatible coating may be replaced or supplemented with a porous, bioactive coating, which may stimulate the formation of osseous tissue, and/or with an antiseptic coating, which may deter or counteract infection at the surface of the implant.

After discectomy (whether complete or partial) and distraction of adjacent elements of a spinal column such as vertebrae (150), prosthesis implantation surgical procedures may involve measurements of intervertebral disc space. These measurements may be used to determine the dimensions and configurations of the upper plate (108), the lower plate (109), and the mobile core (110) to be implanted. In various embodiments, the prosthesis (104) generally may be configured to assist in the correction of various types of spinal disorders, including lordosis and kyphosis. Correction of lordosis or kyphosis may involve imposition of an angle, for example between 0 and 15 degrees, between the upper plate (108) and the lower plate (109) in the postero-anterior direction. The upper plate (108), the lower plate (109), or the core (110) may be configured to assist in imposing such an angle, for example as discussed in U.S. patent application Ser. No. 10/476,565 assigned to the assignee of the present application. In addition, the plates (108, 109) and the core (110) generally have dimensions and configurations selected for the particular patient in which the prosthesis (104) will be implanted. Often, in practice the dimensions and configurations of the prosthesis (104) will not be known until well into the surgical procedure. Accordingly, for any particular patient the surgical staff will need an assortment of prosthesis insertion assembly configurations on hand.

In various embodiments, the plates (108, 109) and core (110) of the prosthesis (104) may be retained by or releasably mounted to an insertion adapter (106). The insertion adapter (106) may be configured in many ways, such as a head, holder, or other carrier of an assembled prosthesis (104), for example. The insertion adapter (106) optionally may have jaws (121) that hold the prosthesis by grasping or pinching the lateral edges of the upper and lower plates of the prosthesis. The insertion adapter (106) may further comprise one or more optional retainers, such as mounting dogs (120). The dogs (120) may engage a respective recess (122) located in the mobile core (110) and contact or grasp a respective one of the posts (124) located on the lower plate (109). The dogs (120) may have surfaces configured to substantially match the spacing and/or configuration of the faces of the recesses (122). One or more of the dogs (120) may be equipped with a channel substantially matching the edge of one of the respective posts (124), to increase the effectiveness of the grasp on the lower plate (109). In addition, the insertion adapter (106) may optionally have additional retaining, grasping, or securing means, for example the illustrated latches (123) disposed on jaws (121), which may engage complementary retaining, grasping, or securing means, such as a receiver, recess, notch, etc., for example the recesses (111) disposed along opposite lateral edges of plate (108).

The insertion adapter (106) in various embodiments also may comprise angled contact surfaces (116) configured for complementary contact with optional angled edges (115) of the prosthesis plates (108, 109). An optional shoulder (118) may be configured for complementary contact with the perimeter of the core (110). The combined height of the contact surfaces (116) and the shoulder (118) may preferably be substantially equal to the distance between the plates (108, 109) of an assembled prosthesis (104). The contact surfaces (116) and the shoulder (118) in various embodiments thus may combine to provide a surface of the insertion adapter (106) complementary to, and substantially fitting, the prosthesis (104) when assembled with, or mounted or attached to, the insertion adapter (106). A complementary fit between angled structures such as this may help stabilize the prosthesis (104) and push its components uniformly into the intervertebral disc space, preventing unwanted rotation or transverse movements of the prosthesis (104) or its components during insertion.

Various embodiments may incorporate any or all of the structures discussed above, but may also have other attachment and support mechanisms. For example, some embodiments optionally may have additional mount points, such as in the upper plate (108), the lower plate (109), or both. Other alternative embodiments could have retainers such as pins or clips that fit into one or more cavities or recesses of various prosthesis components, or one or more of many other methods that could be used to grasp objects and allow for convenient release when desired.

The insertion adapter (106) in various embodiments may have actuator means for releasing the intervertebral this prosthesis (104). In various embodiments, the actuator may be configured as spring-loaded arms, tangs, shanks, or other actuating means (164) articulable about articulating means such as a hinge pin (172). Alternatively, the insertion adapter (106) may have an integral hinge portion about which the arms, tangs, shanks, or other actuating means (164) articulate, for example comprising a flexible material such as plastic or rubber or stress/strain relief features such as cuts or voids. Those of skill in the art, following appreciation of this disclosure, will recognize that many other structural configurations may be devised for the insertion adapter (106) to grasp the intervertebral disc prosthesis (104) and release the intervertebral this prosthesis (104) when inserted in an intervertebral disc space.

Some embodiments of the prosthesis insertion assembly (100) optionally may have a clip (126) that wraps around the assembled prosthesis (104) and holds the plates (108, 109) to the core (110). Retaining means such as the clip (126) augment the insertion adapter (106) in maintaining assembly of the prosthesis (104) during transport and/or during mounting, attaching, or assembling the insertion adapter (106) to or with the insertion tool body (130). Optionally, clip (126) may have one or more removal means to facilitate removal of the clip when the prosthesis insertion assembly (100) is assembled with, or mounted or attached to, an insertion tool body (130), such as tabs (127, 128) on its upper and lower surfaces, respectively, as discussed further below.

In some preferred embodiments, the components of the intervertebral disc prosthesis (104) and the insertion adapter (106) may be sterilized using gamma radiation. Following sterilization, the components may be packaged in primary sterile packaging (103) to form a sterile pack (102), preferably with the components of the intervertebral disc prosthesis (104) and the insertion adapter (106) assembled as an insertion assembly (100), although packaging disassembled components of the intervertebral disc prosthesis (104) and the insertion adapter (106) is within the scope of this invention. In various preferred embodiments, the components of the intervertebral disc prosthesis (104) and the insertion adapter (106) that are packaged in primary sterile packaging (103), whether assembled or disassembled, may be further packaged in a box or other container and enclosed in secondary sterile packaging (103) to form a sterile pack (102). The sterile packaging (103) may comprise bubble packaging, blister packaging, shrink wrapping, or other packaging configuration known to be suitable for maintaining the sterility of a medical implant. Sterile packaging (103) in some embodiments preferably may have an oxygen absorbing packet, for example to reduce the potential for oxidative degradation of a polyethylene core (110) or other components. In preferred embodiments, the sterile pack (102) preferably may be made ready for delivery or transport to a sterile field of a surgical suite, directly or through a distributor.

Sterile packs (102) of insertion assemblies (100) preferably bear identifying information. For example, various embodiments optionally have a package label with identifying information (180). The identifying information may include a use-before-date, the lot number and reference or serial number for the insertion assembly (100) or its components, a sterilization control label, and/or size and configuration information for the plates (108, 109) and the core (110). Preferably, the packaging label allows complete traceability of insertion assembly (100) from initial manufacturing through final implantation and service in a particular patient.

Various embodiments described herein provide a surgical staff with an assortment or other inventory of pre-sterilized, pre-configured, and pre-assembled insertion assemblies (100). Optionally, a packaged intervertebral disc prosthesis insertion assembly may be provided with the intervertebral disc prosthesis (104) disassembled, along with an insertion adapter (106) preconfigured for use with the intervertebral disc prosthesis (104) following its assembly. In such embodiments, the components of the intervertebral disc prosthesis (104) typically would be assembled with the insertion adapter (106) in the sterile field to form an insertion assembly (100).

During a surgical procedure in various embodiments, the surgeon determines the appropriate dimensions and configurations of prosthesis (104). Measurements of the intervertebral disc space may, for example, be used in such a determination. Preferably, the surgical team may obtain the appropriate prosthesis insertion assembly (100) within the sterile field of the surgical suite from an inventory of prosthesis insertion assemblies (100).

In various disclosed embodiments such as shown in FIG. 4, whether providing the intervertebral disc prosthesis (104) assembled or disassembled, the prosthesis insertion assembly (100) may be configured for use with a detachable or demountable tool body (130), which may be used during the surgical procedure to implant the prosthesis (104) in the intervertebral disc space. The prosthesis insertion assembly (100) and the insertion tool body (130) preferably may be arranged or assembled for use, for example by attaching or mounting the prosthesis insertion assembly (100) to an insertion tool body (130), within the sterile field of a surgical suite.

Figure 5A:
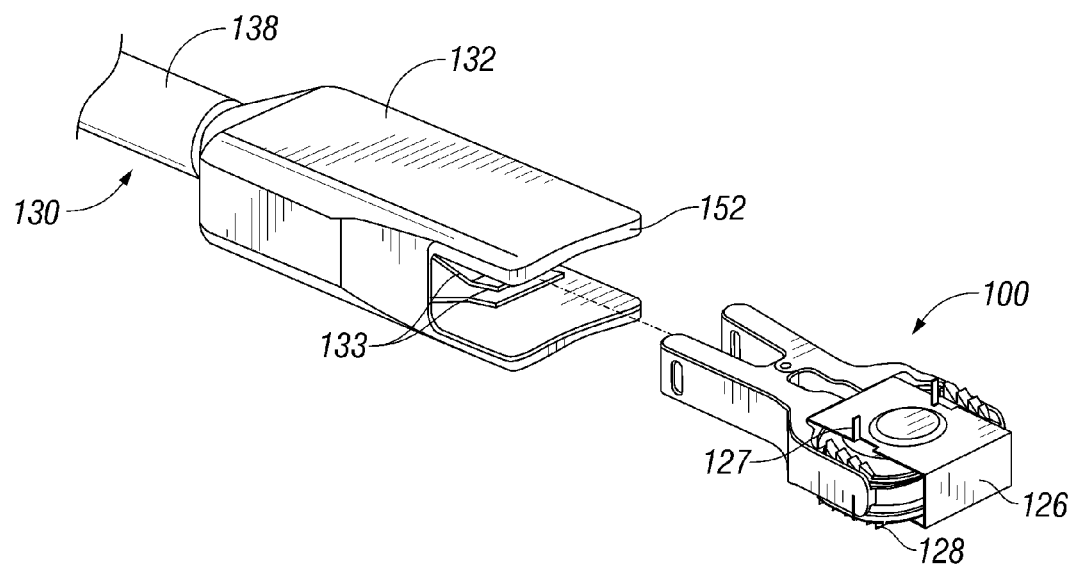
FIGS. 5A and 5b depict components of an insertion tool body and a prosthesis insertion assembly.
Figure 5B:
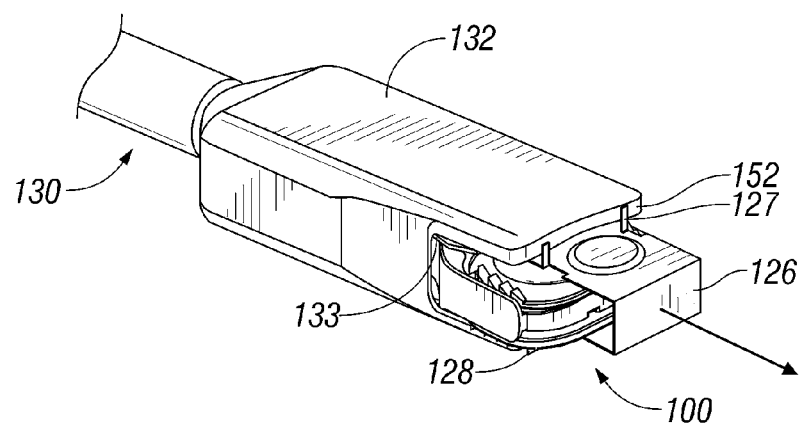

After removal from the sterile pack (102), the insertion assembly (100) and a detachable or demountable insertion tool body (130) are assembled. For the embodiments shown in FIGS. 5A and 5B, the prosthesis insertion assembly (100) may be lined up with a support (132), such as the illustrated housing for example, arranged to receive and support the prosthesis insertion assembly (100) during the implantation procedure. Preferably, the insertion tool body (130) may be adapted for use with all, or at least a wide assortment, of the various dimensions and configurations of intervertebral disc prostheses (104) available. There may be a wide variance in the heights of the various prostheses (104) in some embodiments of intervertebral disc prosthesis delivery and insertion systems. The support (132) optionally may be equipped with one or more retainers, for example the tongues (133) illustrated, to retain the prosthesis components in assembly. Other embodiments that deploy such retainers may use structures such as clips, pawls, springs, or other biasing components. Retainers such as tongues (133) may help center and support a wide variety of prosthesis dimensions and configurations with respect to support (132).

Figure 6A:
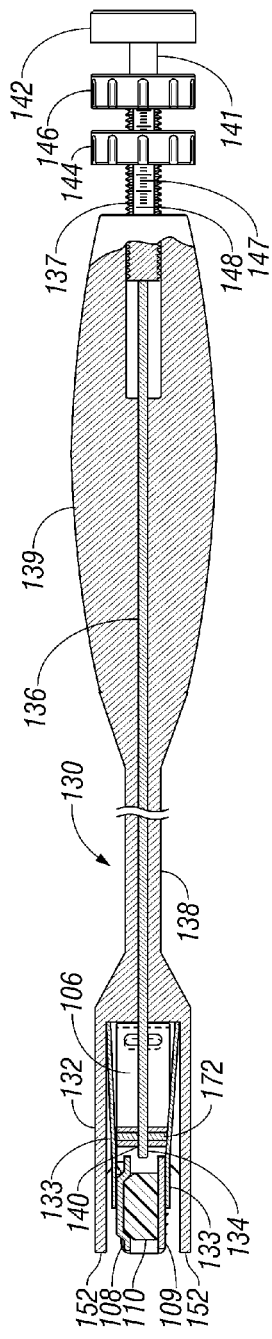
FIGS. 6A, 6B, and 6C depict various views of an insertion tool body.
Figure 6B:
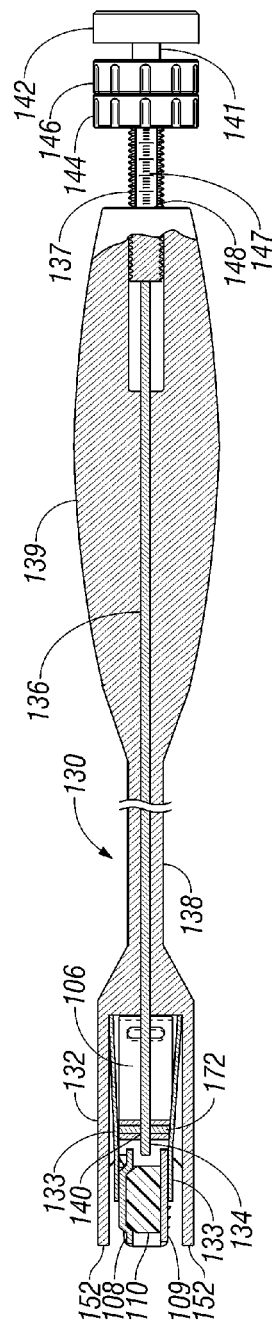
Figure 6C:
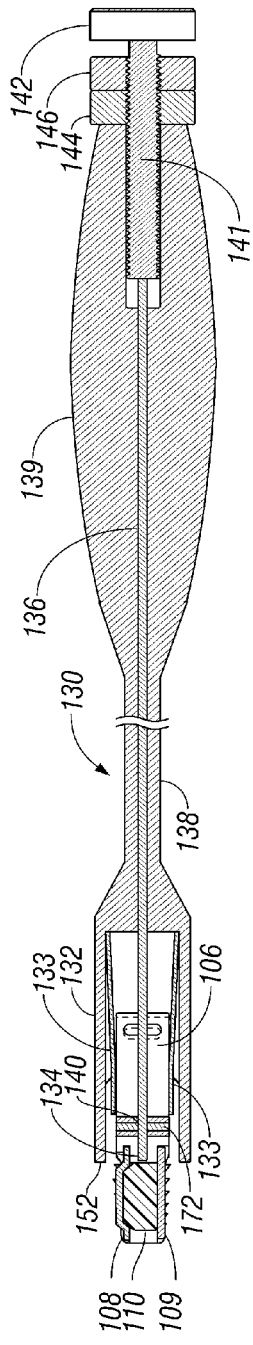

After appreciating the present disclosure, those of skill in the art will readily recognize numerous alternative means of mounting, coupling, assembling, attaching, or otherwise engaging a prosthesis insertion assembly (100) and an insertion tool body (130). For example, the insertion tool body (130) may be equipped with an actuator (136), such as a rod, shaft, cable, or other transmission or control structure, for example as illustrated in FIGS. 6A, 6B, and 6C. The actuator (136) in various embodiments may have engagement means, for example the illustrated threaded end (134) of the rod (136), to engage or connect with a coupler (140), for example the threaded hole illustrated in FIG. 3, of the insertion adapter (106). Once so engaged, the rod (136) may hold and push the insertion adapter (106) during the implantation procedure.

The prosthesis insertion assembly (100) optionally may be attached or mounted to the insertion tool body (130) by engagement of the threaded end (134) with threaded hole (140). The insertion assembly (100) may be disposed by hand at least partially within support (132), at least to the point where the insertion assembly (100) engages the threaded end (134). The insertion assembly (100) may be further disposed by hand fully within support (132), causing the threaded end (134) to recess into the member (138) of the insertion tool body (130). At this point, the threaded end (134) may be rotated in threaded hole (140) until appropriate engagement of the threads is achieved and the prosthesis insertion assembly (100) is firmly retained in support (132). Alternatively, the threaded end (134) may, upon initial engagement with threaded hole (140), be rotated in threaded hole (140) until the prosthesis insertion assembly (100) is drawn fully within and retained in support (132). Regardless of how the prosthesis insertion assembly (100) is disposed into support (132), tabs (127, 128) on the respective upper and lower surfaces clip (126) may be configured to contact leading edges (152) of support (132), respectively, well before the insertion assembly (100) is seated in the insertion assembly (100), causing the clip (126) to detach from the prosthesis (104) as the insertion assembly (100) is further moved into support (132), for example as depicted in FIG. 5.

As shown in FIGS. 6A, 6B, and 6C, for some embodiments the actuator (136) may transit the member (138), which for example may be configured as a frame or shaft as illustrated. The actuator (136) may be equipped with a control at the end the insertion tool body (130) opposite the support (132), such as the knob (142) or a lever, button, or other control structure. In various embodiments, the control (142) may control both the delivery of the insertion adapter (106) and the prosthesis (104) to the intervertebral disc space from the support (132) as well as the release of the insertion adapter (106) from the insertion tool body (130) following such delivery, but separate controls may be provided for each function, and optionally may be provided for other functions. For insertion of the prosthesis (104) in various embodiments, the rod (136) may slide in the member (138) of the insertion tool body (130) toward the support (132) (the insertion direction), thus moving the insertion assembly (100) into the intervertebral disc space. With the insertion assembly (100) moved into the intervertebral disc space, threaded end (134) of rod (136) may be decoupled from the coupler of the insertion adapter (106) and the insertion tool body (130) moved away.

Various embodiments of the insertion tool body (130) may preferably be configured with an adjustable insertion stop to control the distance of the insertion of the intervertebral prosthesis (104) within the intervertebral disc space. FIGS. 6A, 6B, and 6C depict an exemplary adjustable stop configuration. In FIG. 6A, the prosthesis insertion assembly (100) is fully disposed in and firmly retained by support (132), with the threaded end (134) being substantially or fully engaged with threaded hole (140). A scale (147) may be disposed on a planar recess disposed on a shaft or stud (141) integral with or attached to the control knob (142). The scale (147) may be graduated in appropriate units of length and may include a zero mark (148). Tangs (164) and threaded hole (140) of insertion adapter (106) may be dimensioned and configured to accommodate further rotation of threaded end (134) in the threaded hole (140) in the position illustrated by FIG. 6A. Knob (142) may can be adjusted in handle (139) to position the zero mark (148) at an appropriate indicator, such as the end of handle (139) or other form of reference, for example as illustrated in FIG. 6B, which indexes knob (142), shaft or stud (141), rod (136), and the prosthesis insertion assembly (100) in the fully mounted position in support (132).

For various embodiments, when the zero mark (148) is set to the indicator with the prosthesis insertion assembly (100) in the fully mounted position in the support (132), for example as depicted in FIG. 6B, the scale (147) will indicate the distance that the prosthesis insertion assembly (100) has been extended from the support (132) by movement of the rod (136) within member (138) of insertion tool body (130). During the insertion of the intervertebral disc prosthesis (104), the leading edges (152) of the support (132) may be held firmly against respective vertebrae (150) defining the disc space receiving the prosthesis (104), as illustrated for example in FIGS. 8 and 10. Accordingly, the scale (147) can be used to indicate the distance of insertion of the prosthesis (104) within the intervertebral disc space.

Various embodiments may deploy an adjustable stop, for example a threaded nut (144) adjustable along threads (137) of the shaft or stud (141). The adjustable stop (144) may be used to control the distance of insertion of the prosthesis (104) within the intervertebral disc space. In various embodiments, for example, sliding of the rod (136) in the insertion direction will be stopped when the adjustable stop (144) abuts the end of handle (139). A stop lock may be used to maintain the setting of the stop (144), for example by use of a lock nut (146) as illustrated, or by other known locking structures. Preferably, the stop (144) will be adjusted in accordance with the size of the intervertebral disc space, typically measured and analyzed before the insertion stage of the surgical procedure as discussed elsewhere in this disclosure. FIG. 6C depicts an insertion assembly (100) extended from support (132) by a distance controlled by stop (144) abutting handle (139).

Figure 7:
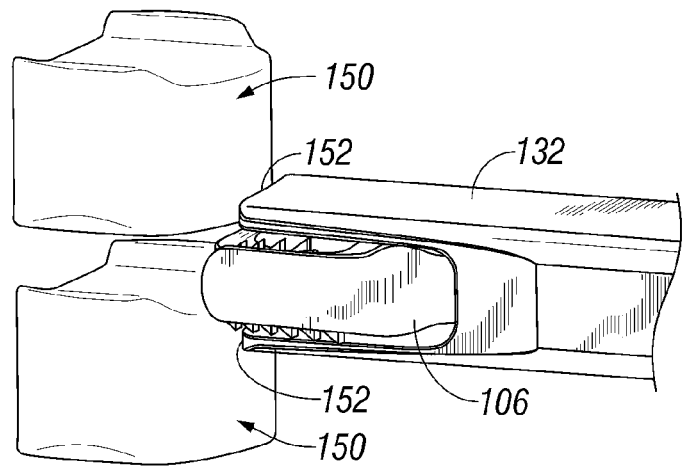
FIG. 7 depicts a prosthesis insertion assembly and a support of an insertion tool body.
Figure 8:
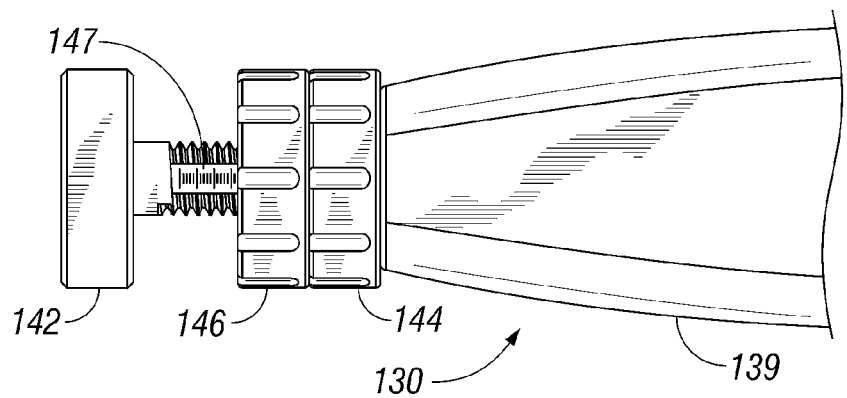
FIG. 8 depicts components and a portion of an insertion tool body.
Figure 9:
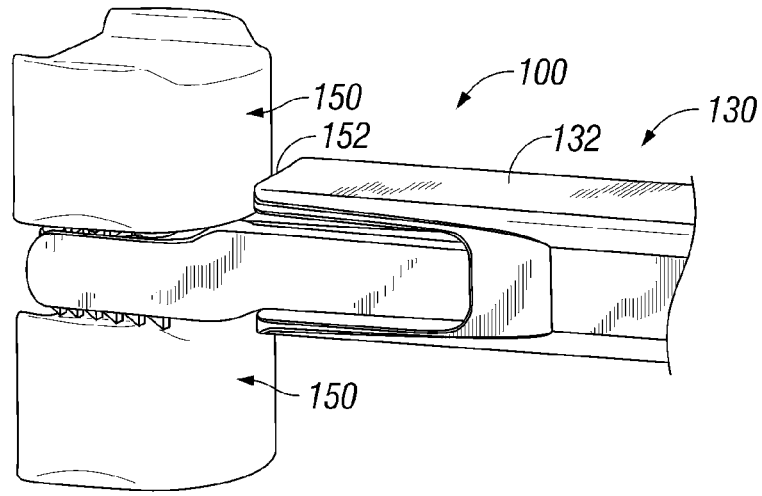
FIG. 9 depicts a prosthesis insertion assembly and a support of an insertion tool body.
Figure 10:
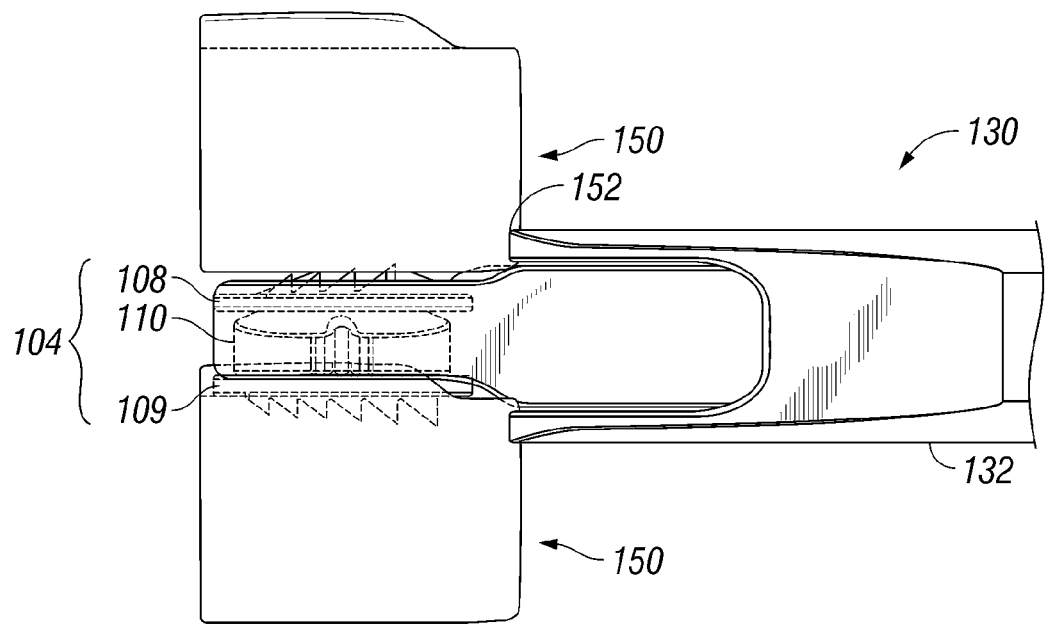
FIG. 10 depicts a prosthesis insertion assembly and a support of an insertion tool body.

FIG. 7 illustrates the commencement of the insertion stage of an embodiment of a surgical procedure. The insertion tool (130) and the prosthesis insertion assembly (100) may be configured and adjusted in accordance with the discussion above. The insertion tool (130) and the insertion assembly (100) may be located in the desired prosthesis insertion axis and located to place the leading edges (152) of the support (132) in contact with the respective vertebrae (150) defining the intervertebral disc space receiving the prosthesis (104). In various embodiment, the surgeon may apply force to the knob (142) by pressing it or striking it with a soft mallet or by hand. Force may be applied until the stop (144) abuts the end of the handle (139), as shown in FIG. 8. When the stop (144) abuts the end of the handle (139), the end (134) of the rod (136) will have pushed the insertion adapter (106) into position where the prosthesis (104) is properly positioned in the intervertebral disc space between the vertebrae (150). FIGS. 9 and 10 provide a representative illustration of the final positioning at this stage.

Figure 11:
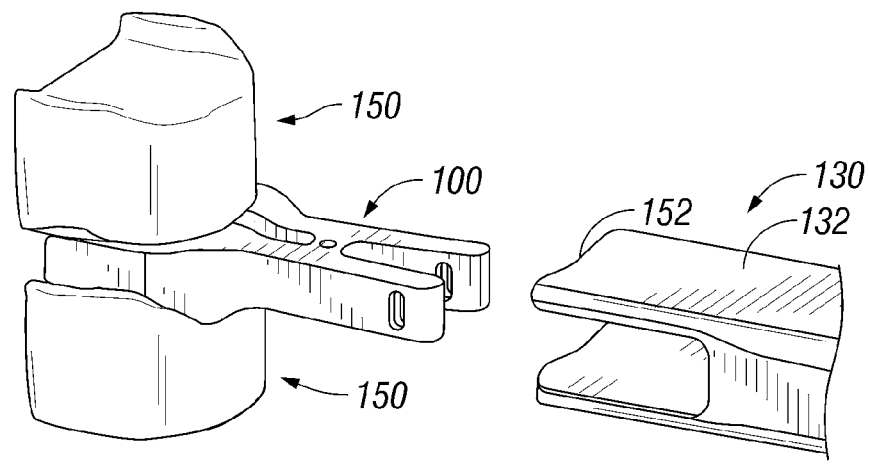
FIG. 11 depicts a prosthesis insertion assembly and a support of an insertion tool body.
Figure 12:
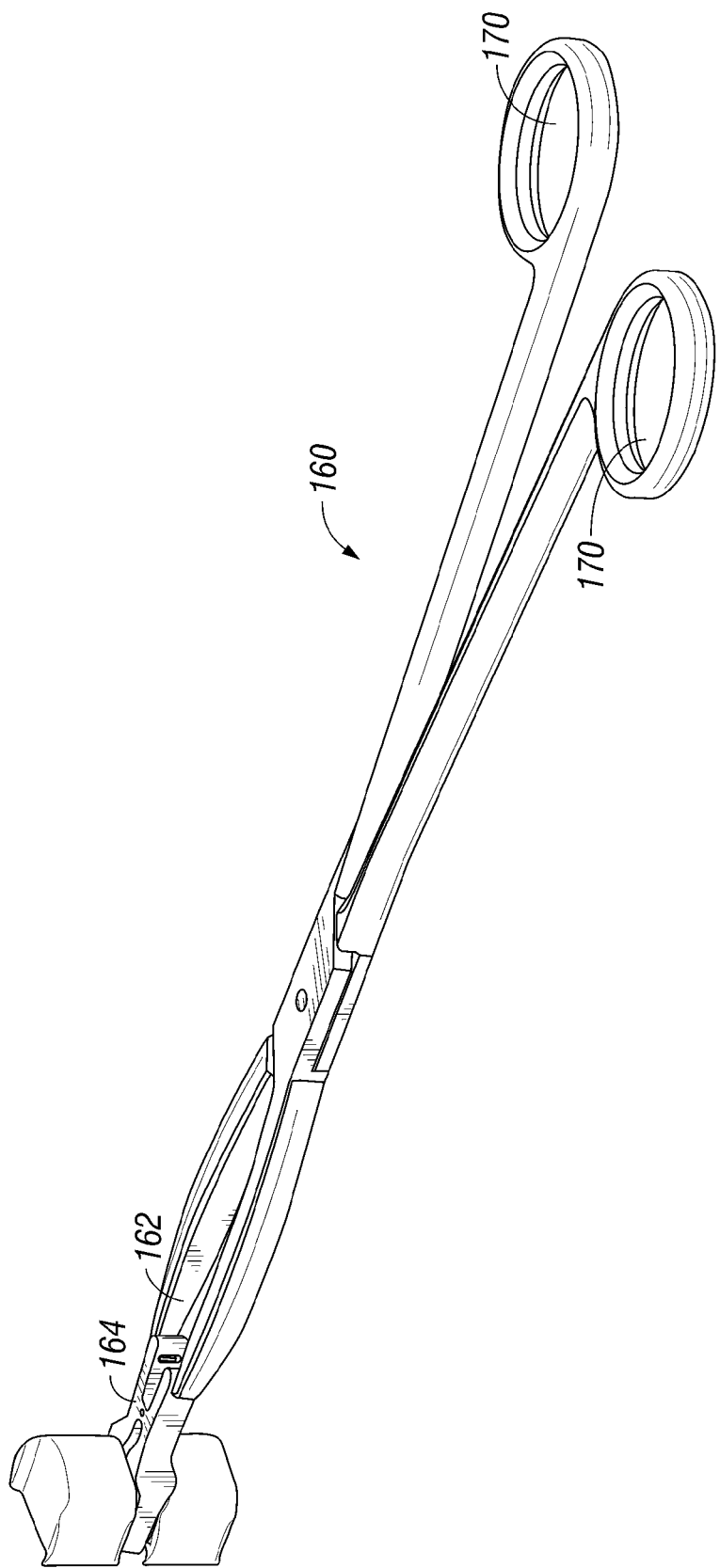
FIG. 12 depicts a removal tool.
Figure 13:
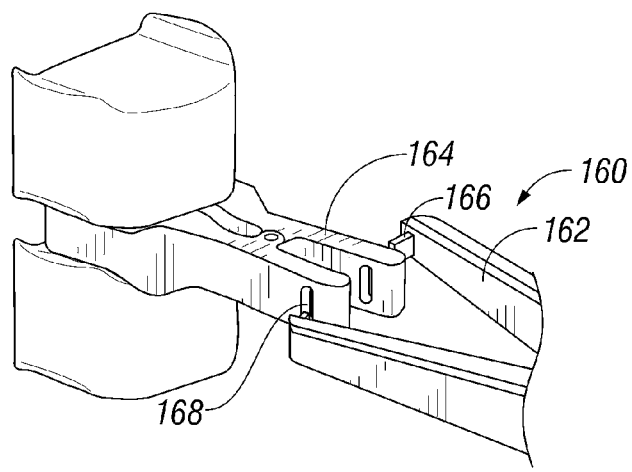
FIG. 13 depicts a prosthesis insertion assembly and a removal tool.
Figure 14:
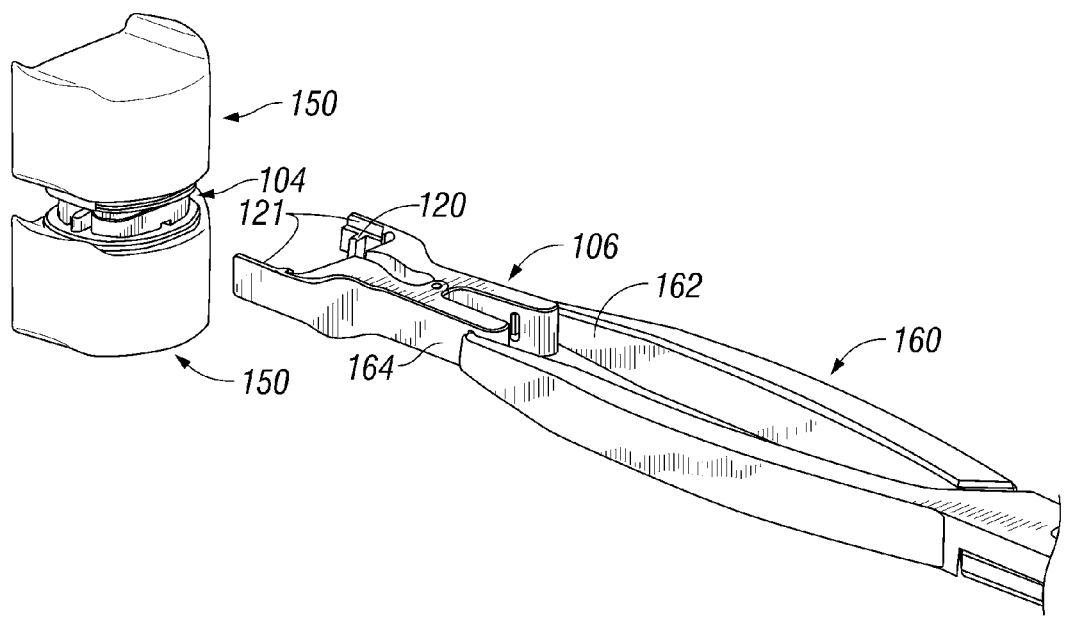
FIG. 14 depicts an intervertebral disc prosthesis, insertion adapter, and a removal tool.

For various embodiments, the insertion tool body (130) may be detached or demounted from the insertion assembly (100) by rotating the knob (142) counter-clockwise until the threaded end (134) releases from the threaded hole (140). FIG. 11 shows the insertion tool body (130) as it is being withdrawn, leaving only the insertion assembly (100) in the opening between the vertebrae (150). A removal tool (160), for example as shown in FIG. 12, may be used to separate the insertion adapter (106) from the prosthesis 104, leaving the prosthesis (104) implanted in the intervertebral disc space. FIG. 13 shows the removal tool (160) approaching the insertion adapter (106). Tool ends (162) of the removal tool (160) may be positioned along the tangs (164) of the insertion adapter (106) in such a way that pins (166) enter slots (168) disposed in the tangs (164). Other embodiments may include a single hole in each tang (164), multiple smaller holes or slots, or any of many other means for the removal tool (160) to attach with, connect to, or latch on the tangs (164) of the insertion adapter (106). Actuating a removal tool (160) by squeezing handles (170) of the removal tool (160) may pivot the tangs (164) of the insertion adapter (106) around the hinge pin (172), causing the jaws (121) to release the plates and the mounting dogs (120) to release their grip on the posts (124) and disengage from the recesses (122). In alternative embodiments of insertion adapter (106) comprising a flexible portion at which the tangs (164) articulate, squeezing the tangs (164) will cause the flexible body to flex, the tangs (164) to articulate, the jaws (121) to release the plates, and the mounting dogs (120) to release their grip on the posts (124) and disengage from the recesses (122). Once the insertion adapter (106) releases the prosthesis (104), the insertion adapter (106) may be removed, for example as shown in FIG. 14, leaving the prosthesis (104) properly positioned in the disc space between the two vertebrae (150).

Figure 15:
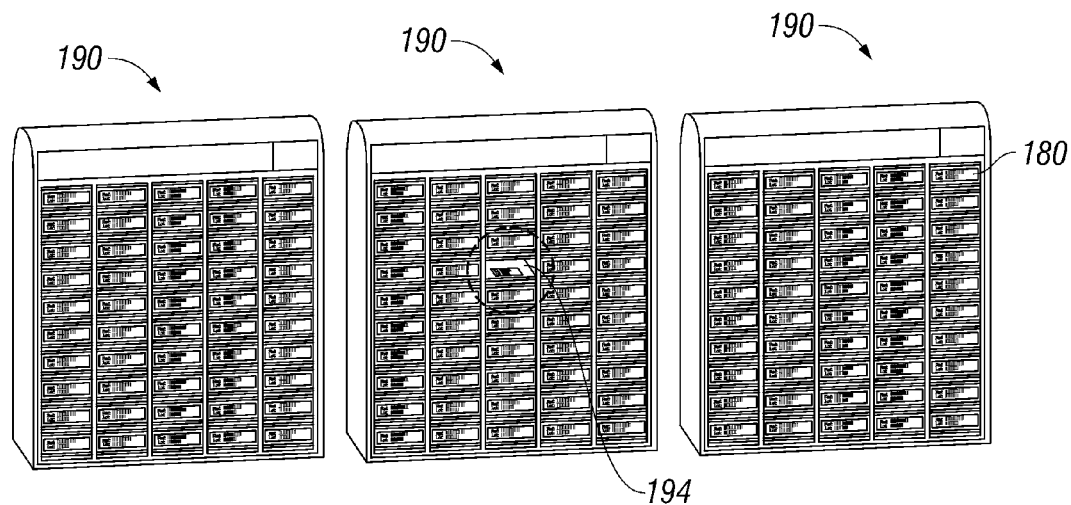
FIG. 15 depicts inventory storage space and a storage location.

Various embodiments of an intervertebral disc prosthesis delivery and insertion system also may be provided. In a preferred embodiment, the sterile pack (102) inventory may be maintained in dedicated inventory storage space, for example racks (190) as illustrated in FIG. 15. Various embodiments may have prostheses each configured with a first plate having a size and configuration selected from a set of first size and configuration specifications, a second plate having a size and configuration selected from a set of second size and configuration specifications, and a core having a size and configuration selected from a set of third size and configuration specifications. The first plate, the second plate, and/or the core configuration optionally may specify a lordosis or kyphosis correction. In various embodiments, any of the sets of size and configuration specifications may contain only one element, in which case the particular component may be provided in only one size and configuration.

Preferably, the inventory will be organized by plate dimension, core height, and lordosis/kyphosis correction angle (if any), but other characteristics of the prostheses (104) may be used for an organizational scheme. Each rack (190), for example, may contain insertion assemblies (100) of various dimensions all having a particular lordosis/kyphosis correction angle, with the sterile packs (102) organized in the respective racks (190) in rows by the plate dimension and in columns by the core height of the packaged prostheses (104). Alternatively, any organization scheme using any combination of the set of first size and configuration specifications, the set of second size and configuration specifications, and/or the third size and configuration specifications may be used. Preferably, each storage location (194) corresponds to one of the selected combinations of first size and configuration specifications, second size and configuration specifications, and/or third size and configuration specifications.

As noted above, in various embodiments the sterile packs (102) of insertion assemblies (100) preferably bear identifying information. For example, various embodiments optionally have a package label with identifying information (180). The label (180) disposed on a sterile pack (102) preferably will indicate the enclosed prosthesis's plate dimension, core height, and lordosis/kyphosis correction angle (if any), along with the stock-keeping unit (SKU) designation of the sterile pack (102) and the other information discussed above, some or all of which preferably may be encoded in scannable code included on the label or other component of the packaging, for example a chip or transponder. Other information (180) optionally may be provided, for example further logistical management information such as inspection data, reorder points, lead times, etc., or information relevant to surgical techniques and equipment. Coding can be done with bar or other optical codes, magnetic stripes, radio-frequency identification, or other known techniques. The identifying information (180) on a sterile pack (102) preferably may be readable when insertion assembly (100) is stocked in the rack.

Figure 16:
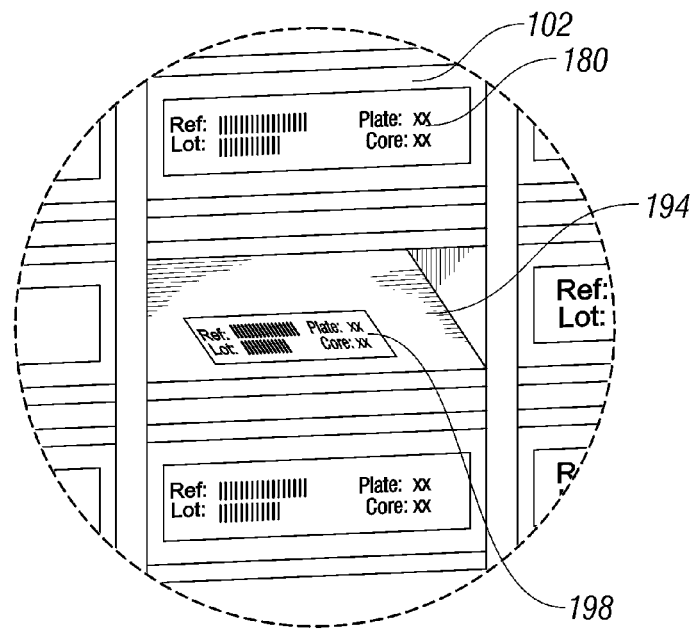
FIG. 16 depicts a storage location and configuration information.

The sterile pack (102) storage locations, for example bins (194) of the racks (190), optionally each may contain a label having identifying information for the sterile pack (102) that should be stocked in that bin (194), for example as depicted in FIG. 16. Other means of providing the information about the sterile pack (102) that should be stored in the bin (194), of course, may be use, for example magnetic stripes, radio-frequency identification, or other known techniques. Preferably, each bin label (194) or other form of identifying information may be readable when the respective bin (194) is empty. Thus, stock keeping may be simplified by providing sufficient information for re-ordering from routine observation of empty rack spaces, and acquisition of the correct assembly (100) during surgery may be simplified by the rack's organizational scheme. Stock keeping and insertion assembly (100) acquisition can be further enhanced by providing label- or other information-scanning equipment in the sterile field of the surgical suite, which will provide another level of verification of sterile pack (102) ordering and acquisition.

After appreciating this disclosure, those of skill in the art will recognize that other logistical management techniques advantageously can be applied to the intervertebral disc prosthesis delivery and insertion systems and methods disclosed herein.

Figure 17:
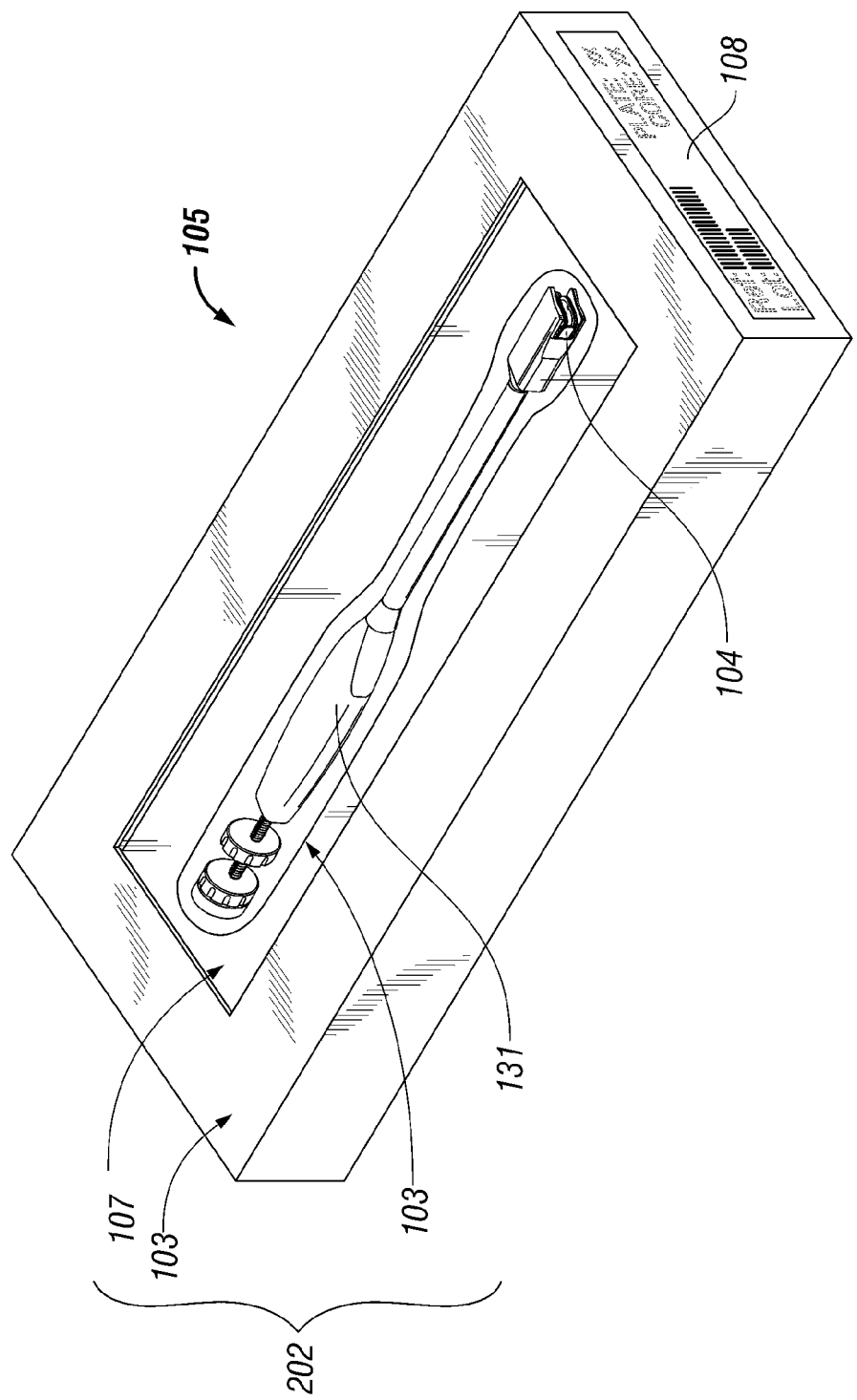
FIG. 17 depicts a sterile pack comprising a prosthesis insertion assembly.

Various features of embodiments of a packaged intervertebral disc prosthesis insertion assembly (101) comprising a sterile insertion adapter (106) and sterile components of an intervertebral disc prosthesis (104) are described above. Those of skill in the art will recognize after appreciating this disclosure that similar features may be provided in embodiments of a packaged intervertebral disc prosthesis insertion assembly (105) comprising a sterile insertion tool (131) and sterile components of an intervertebral disc prosthesis (104). For example, as shown in FIG. 17 the sterile insertion tool (131) and the sterile intervertebral disc prosthesis (104) may be assembled together and disposed in primary, or inner, sterile packaging (103) and in secondary, or outer, sterile packaging (103) to form a sterile pack (202). The components of the intervertebral disc prosthesis (104) in this embodiment may be assembled with the sterile insertion tool (131) and provided to the sterile field of a surgical suite pre-configured and ready to use. The sterile insertion tool (131) optionally may have an insertion tool body (130) and a detachable insertion adapter (106), which may be packaged assembled or disassembled. Alternatively, the sterile insertion tool (131) may have an insertion adapter (106) integral with an insertion tool body (130), or the sterile insertion tool (131) may have other structures devised to hold the intervertebral disc prosthesis (104) and/or deliver it to the intervertebral disc space. Various features of the insertion adapter (106) and/or the insertion tool body (130) discussed above, and/or the various components of the foregoing and other components discussed above, optionally may be included for the packaged intervertebral disc prosthesis insertion assembly (105). Various features the intervertebral disc prosthesis delivery and insertion systems discussed above, as well as features of other systems, optionally may also be used with a packaged intervertebral disc prosthesis insertion assembly (105) comprising a sterile insertion tool (131) and sterile components of an intervertebral disc prosthesis (104).

Those of skill in the art will recognize after appreciating this disclosure that the steps of the various methods, processes, and other techniques disclosed herein need not be performed in any particular order, unless otherwise expressly stated or logically necessary to satisfy expressly stated antecedent conditions. In addition, after appreciating this disclosure those skilled in the art will recognize that the invention may be embodied in a variety of different forms and that various changes, substitutions, and alterations can be made without departing from the spirit and scope of the invention. The described embodiments are illustrative only and are not restrictive, and the scope of the invention is defined solely by the following claims.

The invention claimed is:

1. A device for treatment of an intervertebral space between two adjacent vertebrae comprising:
an intervertebral prosthesis comprising
a first plate having a first edge, a second edge, and a first surface configured for contact with a first vertebra, the first surface disposed between the first and second edges of the first plate, and
a second plate having a first edge, a second edge, and a second surface configured for contact with a second vertebra, the second surface disposed between the first and second edges of the second plate;
a prosthesis insertion adapter comprising
a first arm comprising a first jaw configured to hold the first edge of the first plate and the first edge of the second plate, and a first tang disposed at an opposite end of the first arm from the first jaw,
a second arm comprising a second jaw configured to hold the second edge of the first plate and the second edge of the second plate, and a second tang disposed at an opposite end of the second arm from the second jaw, an articulation between the first arm and the second arm, the articulation disposed between the first jaw and the first tang and between the second jaw and the second tang, and a coupler configured for operationally releasable attachment of the insertion adapter to an implantation tool; and an elongated implantation tool comprising a prosthesis insertion adapter support disposed at a first end of the tool, the insertion adapter support comprising a connector attachable to the insertion adapter coupler, and an operating handle disposed at a second end of the tool, the operating handle comprising a control operable to release the connector from the insertion adapter coupler;

the device having an unassembled configuration in which the prosthesis is gripped by the first jaw and the second jaw, the coupler is detached from the connector, and the implantation tool is detached from the insertion adapter, and an assembled configuration in which the prosthesis is gripped by the first jaw and the second jaw, the coupler is attached to the connector, and the implantation tool and the insertion adapter are connected.

2. The device of claim 1 in which a dog protrudes from at least one of the first and second arms.

3. The device of claim 2 in which the intervertebral prosthesis comprises a core, and the core comprises a recess disposed along a side of the core, with the dog engaging the recess when the device is in the assembled configuration.

4. The device of claim 3 in which the at least one of the first and second plates comprises a protruding post, and the dog contacts the post when the device is in the assembled configuration.

5. The device of claim 4 in which the recess has opposing faces, and the dog comprises surfaces substantially matching the spacing of the opposing faces of the recess.

6. The device of claim 5 in which the post has an edge having a contour, and the dog comprises a channel substantially matching the contour of the edge.

7. The device of claim 6 in which the dog at least partially occupies the recess when the device is in the assembled configuration.

8. The device of claim 7 in which the edge of the post at least partially occupies the channel when the device is in the assembled configuration.

9. The device of claim 1 in which the first edge of the first plate comprises a first recess and the first arm comprises a first latch, with the first recess and the first latch configured for the first latch to occupy the first recess when the device is in the assembled configuration.

10. The device of claim 9 in which the second edge of the first plate comprises a second recess and the first arm comprises a second latch, with the second recess and the second latch configured for the second latch to occupy the second recess when the device is in the assembled configuration.

11. The device of claim 1 in which the first arm comprises a contact surface configured for complementary contact with at least a portion of the first edge of the first plate when the device is in the assembled configuration.

12. The device of claim 11 further comprising a core having a perimeter and a shoulder disposed on the first arm, with the shoulder configured for complementary contact with at least a portion of the core when the device is in the assembled configuration.

13. The device of claim 12 in which the contact surface and the shoulder have a combined height that is substantially equal to a distance between the first plate and the second plate when the device is in the assembled configuration.

14. The device of claim 13 in which the contact surface and the shoulder substantially fit against portions of the first plate, the second plate, and the core when the device is in the assembled configuration.

15. The device of claim 1 in which the articulation comprises a protrusion on the first arm placed within a recess on the second arm when the device is in the assembled configuration.

16. The device of claim 15 in which the protrusion and the recess are traversed by a pin when the device is in the assembled configuration.

17. The device of claim 1 in which the articulation is biased by a spring.

18. The device of claim 1 in which the articulation is configured so that movement of the first arm toward the second arm causes the first jaw to move away from the second jaw.

19. The device of claim 1 in which the first plate comprises a first array of anchors disposed on the first surface of the first plate along the first edge of the first plate, and a second array of anchors disposed on the first surface of the first plate along the second edge of the first plate.

20. The device of claim 19 in which each anchor of the first array has a height, the height of each anchor of the first array differs from the height of each other anchor of the first array, and the anchors of the first array are arranged in a row with such heights increasing from one end of the row to the other.

* * * * *